United States Patent
Kapeller-Libermann et al.

(10) Patent No.: US 6,607,892 B2
(45) Date of Patent: Aug. 19, 2003

(54) 21529, A NOVEL ADENYLATE CYCLASE

(75) Inventors: Rosana Kapeller-Libermann, Chestnut Hill, MA (US); Miyoung Chun, Belmont, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/121,911

(22) Filed: Apr. 12, 2002

(65) Prior Publication Data

US 2002/0164632 A1 Nov. 7, 2002

Related U.S. Application Data

(62) Division of application No. 09/412,210, filed on Oct. 5, 1999, now Pat. No. 6,403,358.

(51) Int. Cl.$^7$ .................. G01N 33/53; C12Q 1/527; C12N 9/88
(52) U.S. Cl. ................. 435/7.1; 435/4; 435/232
(58) Field of Search ................. 435/4, 7.1, 232

(56) References Cited

U.S. PATENT DOCUMENTS 6,107,076 A * 8/2000 Tang et al. ................ 435/232

FOREIGN PATENT DOCUMENTS

| WO | WO 96/08260 | 3/1996 |
|---|---|---|
| WO | WO 99/01547 | 1/1999 |

OTHER PUBLICATIONS

Chabardes, D. et al., "Localization of mRNAs Encoding Ca$^{2+}$ –Inhibitable Adenyl Cyclases Along the Renal Tubule," *The Journal of Biological Chemistry*, Aug. 1996, pp. 19264–19271, vol. 271, No. 32.

Cooper, D.M., et al., PubMed Abstract, "Adenyl Cyclases and the Interaction Between Calcium and cAMP Signalling," *Nature*, Mar. 30, 1995, pp. 421–424, vol. 374, No. 6521.

Gao, B.N. et al, "Cloning and Expression of a Widely Distributed (Type IV) Adenyl Cyclase," *Proc. Natl. Acad. Sci. USA*, 1991, pp. 10178–10182, vol. 88, No. 22.

Hillier et al., EMBL Accession No. AA044876, Sep. 6, 1996.

Hillier et al., GenBank Accession No. AA044828, Sep. 5, 1996.

Hillier et al., EMBL Accession No. W69778 , Jun. 18, 1998.

Stevens, T. et al., PubMed Abstract, "Ca(2+)–Inhibitable Adenyl Cyclase Modulates Pulmonary Artery Endothelial Cell cAMP Content and Barrier Function," *Proc. Natl Acad Sci USA* , Mar. 28, 1995, pp. 2696–2700, vol. 92, No. 7.

Strausberg et al., GenBank Accession No. AI421810, Mar. 30, 1999.

Warner, D.R. et al., PubMed Abstract, "Cell–Free Synthesis of Functional Type IV Adenyl Cyclase", *Anal Biochem,*, Nov. 20, 1995, pp. 31–36, vol.. 232, No. 1.

Woessner et al., EMBL Accession No. AF088070, Sep. 9, 1998.

Swiss–Prot Entry P26770 (Aug. 1, 1992).
Swiss–Prot Entry Q08462 (Oct. 1, 1994).
Swiss–Prot Entry Q08828 (Oct. 1, 1994).

* cited by examiner

*Primary Examiner*—Elizabeth Slobodyansky
(74) *Attorney, Agent, or Firm*—Millennium Pharmaceuticals, Inc.

(57) ABSTRACT

Novel adenylate cyclase polypeptides, proteins, and nucleic acid molecules are disclosed. In addition to isolated, full-length adenylate cyclase proteins, the invention further provides isolated adenylate cyclase fusion proteins, antigenic peptides, and anti-adenylate cyclase antibodies. The invention also provides adenylate cyclase nucleic acid molecules, recombinant expression vectors containing a nucleic acid molecule of the invention, host cells into which the expression vectors have been introduced, and nonhuman transgenic animals in which an adenylate cyclase gene has been introduced or disrupted. Diagnostic, screening, and therapeutic methods utilizing compositions of the invention are also provided.

9 Claims, 17 Drawing Sheets

Input file 21529cons; Output File 21529tra
Sequence length 3518

CTTCTACAATCGGGGTTTGAGGAAGAAGAAGAAAAGGACTGAAGGATCCCTTCATCGCCAGCTGGAAGCGGGCTTGGGA
GCCCGCAAGGAGGGCCTGAAAAAGAAGACGGGATTGCCACAAGGTTGGGGGCGCGGGGTGGTACGGCTTTGAGCGGGTG
AGAAAAGCTCAGGTGGGGCCCGCCGGGCCGAAGGAGGTAACCCGGCGCCCGGCCCTAGCCAGCCCCGGGGCTCGGGGCT

```
              M   A   R   L   F   S   P   R   P   P   P   S   E   D   L   F   Y    17
GGGGAGATC    ATG GCC CGC CTC TTC AGC CCC CGG CCG CCC CCC AGC GAA GAC CTC TTC TAC    51
  E   T   Y   Y   S   L   S   Q   Q   Y   P   L   L   L   L   L   L   G   I   V    37
 GAG ACC TAC TAC AGC CTG AGC CAG CAG TAC CCG CTG CTG CTG CTG CTG CTG GGG ATC GTG   111
  L   C   A   L   A   A   L   L   A   V   A   W   A   S   G   R   E   L   T   S    57
 CTC TGT GCG CTC GCG GCG CTG CTC GCA GTG GCC TGG GCC AGC GGC AGG GAG CTG ACC TCA   171
  D   P   S   F   L   T   T   V   L   C   A   L   G   G   F   S   L   L   L   G    77
 GAC CCG AGC TTC CTG ACC ACT GTG CTG TGC GCG CTG GGC GGC TTC TCG CTG CTG CTG GGC   231
  L   A   S   R   E   Q   R   L   Q   R   W   T   R   P   L   S   G   L   V   W    97
 CTC GCT TCC CGG GAG CAG CGA CTG CAG CGC TGG ACG CGT CCC CTG TCC GGC TTG GTA TGG   291
  V   A   L   L   A   L   G   H   A   F   L   F   T   G   G   V   V   S   A   W   117
 GTC GCG CTG CTA GCG CTA GGC CAC GCC TTC CTG TTC ACC GGG GGC GTG GTG AGC GCC TGG   351
  D   Q   V   S   Y   F   L   F   V   I   F   T   A   Y   A   M   L   P   L   G   137
 GAC CAG GTG TCC TAT TTT CTC TTC GTC ATC TTC ACG GCG TAT GCC ATG CTG CCC TTG GGC   411
  M   R   D   A   A   V   A   G   L   A   S   S   L   S   H   L   L   V   L   G   157
 ATG CGG GAC GCC GCC GTC GCG GGC CTC GCC TCC TCA CTC TCG CAT CTG CTG GTC CTC GGG   471
  L   Y   L   G   P   Q   P   D   S   R   P   A   L   L   P   Q   L   A   A   N   177
 CTG TAT CTT GGG CCA CAG CCG GAC TCA CGG CCT GCA CTG CTG CCG CAG TTG GCA GCA AAC   531
  A   V   L   F   L   C   G   N   V   A   G   V   Y   H   K   A   L   M   E   R   197
 GCA GTG CTG TTC CTG TGC GGG AAC GTG GCA GGA GTG TAC CAC AAG GCG CTG ATG GAG CGC   591
  A   L   R   A   T   F   R   E   A   L   S   S   L   H   S   R   R   R   L   D   217
 GCC CTG CGG GCC ACG TTC CGG GAG GCA CTC AGC TCC CTG CAC TCA CGC CGG CGG CTG GAC   651
  T   E   K   K   H   Q   E   H   L   L   L   S   I   L   P   A   Y   L   A   R   237
 ACC GAG AAG AAG CAC CAA GAA CAC CTT CTC TTG TCC ATC CTT CCT GCC TAC CTG GCC CGA   711
  E   M   K   A   E   I   M   A   R   L   Q   A   G   Q   G   S   R   P   E   S   257
 GAG ATG AAG GCA GAG ATC ATG GCA CGG CTG CAG GCA GGA CAG GGG TCA CGG CCA GAG AGC   771
  T   N   N   F   H   S   L   Y   V   K   R   H   Q   G   V   S   V   L   Y   A   277
 ACT AAC AAT TTC CAC AGC CTC TAT GTC AAG AGG CAC CAG GGA GTC AGC GTG CTG TAT GCT   831
  D   I   V   G   F   T   R   L   A   S   E   C   S   P   K   E   L   V   L   M   297
 GAC ATC GTG GGC TTC ACG CGG CTG GCC AGC GAG TGT TCC CCT AAG GAG CTG GTG CTC ATG   891
  L   N   E   L   F   G   K   F   D   Q   I   A   K   E   H   E   C   M   R   I   317
 CTC AAT GAG CTC TTT GGC AAG TTC GAC CAG ATT GCC AAG GAG CAT GAA TGC ATG CGG ATC   951
  K   I   L   G   D   C   Y   Y   C   V   S   G   L   P   L   S   L   P   D   H   337
 AAG ATC CTG GGG GAC TGT TAC TAC TGT GTC TCT GGG CTG CCA CTC TCA CTG CCA GAC CAT  1011
  A   I   N   C   V   R   M   G   L   D   M   C   R   A   I   R   K   L   R   A   357
 GCC ATC AAC TGC GTG CGC ATG GGC CTG GAC ATG TGC CGG GCC ATC AGG AAA CTG CGG GCA  1071
  A   T   G   V   D   I   N   M   R   V   G   V   H   S   G   S   V   L   C   G   377
 GCC ACT GGC GTG GAC ATC AAC ATG CGT GTG GGC GTG CAC TCA GGC AGC GTA CTG TGT GGA  1131
```

FIG. 1A.

```
      V   I   G   L   Q   K   W   Q   Y   D   V   W   S   H   D   V   T   L   A   N    397
     GTC ATC GGG CTG CAG AAG TGG CAG TAC GAC GTT TGG TCA CAT GAT GTC ACA CTG GCT AAC   1191
      H   M   E   A   G   G   V   P   G   R   V   H   I   T   G   A   T   L   A   L    417
     CAC ATG GAG GCA GGC GGT GTA CCA GGG CGA GTG CAC ATC ACA GGG GCT ACC CTG GCC CTG   1251
      L   A   G   A   Y   A   V   E   D   A   G   M   E   H   R   D   P   Y   L   R    437
     CTG GCA GGG GCT TAT GCT GTG GAG GAC GCA GGC ATG GAG CAT CGG GAC CCC TAC CTT CGG   1311
      E   L   G   E   P   T   Y   L   V   I   D   P   R   A   E   E   E   D   E   K    457
     GAG CTA GGG GAG CCT ACC TAT CTG GTC ATC GAT CCA CGG GCA GAG GAG GAG GAT GAG AAG   1371
      G   T   A   G   G   L   L   S   S   L   E   G   L   K   M   R   P   S   L   L    477
     GGC ACT GCA GGA GGC TTG CTG TCC TCG CTT GAG GGC CTC AAG ATG CGT CCA TCA CTG CTG   1431
      M   T   R   Y   L   E   S   W   G   A   A   K   P   F   A   H   L   S   H   G    497
     ATG ACC CGT TAC CTG GAG TCC TGG GGG GCA GCC AAG CCT TTT GCC CAC CTG AGC CAC GGA   1491
      D   S   P   V   S   T   S   T   P   L   P   E   K   T   L   A   S   F   S   T    517
     GAC AGC CCT GTG TCC ACC TCC ACC CCT CTC CCG GAG AAG ACC CTG GCT TCC TTC AGC ACC   1551
      Q   W   S   L   D   R   S   R   T   P   R   G   L   D   D   E   L   D   T   G    537
     CAG TGG AGC CTG GAT CGG AGC CGT ACC CCC CGG GGA CTA GAT GAT GAA CTG GAC ACC GGG   1611
      D   A   K   F   F   Q   V   I   E   Q   L   N   S   Q   K   Q   W   K   Q   S    557
     GAT GCC AAG TTC TTC CAG GTC ATT GAG CAG CTC AAC TCG CAG AAA CAG TGG AAG CAG TCG   1671
      K   D   F   N   P   L   T   L   Y   F   R   E   K   E   M   E   K   E   Y   R    577
     AAG GAC TTC AAC CCA CTG ACA CTG TAC TTC AGA GAG AAG GAG ATG GAG AAA GAG TAC CGA   1731
      L   S   A   I   P   A   F   K   Y   Y   E   A   C   T   F   L   V   F   L   S    597
     CTC TCT GCA ATC CCC GCC TTC AAA TAC TAT GAA GCC TGC ACC TTC CTG GTT TTT CTC TCC   1791
      N   F   I   I   Q   M   L   V   T   N   R   P   P   A   L   A   I   T   Y   S    617
     AAC TTC ATC ATC CAG ATG CTA GTG ACA AAC AGG CCC CCA GCT CTG GCC ATC ACG TAT AGC   1851
      I   T   F   L   L   F   L   L   I   L   F   V   C   F   S   E   D   L   M   R    637
     ATC ACT TTC CTC CTC TTC CTC CTC ATC CTT TTT GTC TGC TTC TCA GAG GAC CTG ATG AGG   1911
      C   V   L   K   G   P   K   M   L   H   W   L   P   A   L   S   G   L   V   A    657
     TGT GTC CTG AAA GGC CCC AAG ATG CTG CAC TGG CTG CCT GCA CTG TCT GGC CTG GTG GCC   1971
      T   R   P   G   L   R   I   A   L   G   T   A   T   I   L   L   V   F   A   M    677
     ACA CGA CCA GGA CTG AGA ATA GCC TTG GGC ACC GCC ACC ATC CTC CTT GTC TTT GCC ATG   2031
      A   I   T   S   L   F   F   F   P   T   S   S   D   C   P   F   Q   A   P   N    697
     GCC ATT ACC AGC CTG TTC TTC TTC CCA ACA TCA TCA GAC TGC CCT TTC CAA GCT CCC AAT   2091
      V   S   S   M   I   S   N   L   S   W   E   L   P   G   S   L   P   L   I   S    717
     GTG TCC TCC ATG ATT TCC AAC CTC TCC TGG GAG CTC CCT GGG TCT CTG CCT CTC ATC AGT   2151
      V   P   Y   S   M   H   C   C   T   L   G   F   L   S   C   S   L   F   L   H    737
     GTC CCA TAC TCC ATG CAC TGC TGC ACG CTG GGC TTC CTC TCC TGC TCC CTC TTT CTG CAC   2211
      M   S   F   E   L   K   L   L   L   L   L   W   L   A   A   S   C   S   L        757
     ATG AGC TTC GAG CTG AAG CTG CTG CTG CTC CTG CTG TGG CTG GCG GCA TCC TGC TCC CTC   2271
      F   L   H   S   H   A   W   L   S   E   C   L   I   V   R   L   Y   L   G   P    777
     TTC CTG CAC TCC CAT GCC TGG CTG TCG GAA TGC CTC ATC GTC CGC CTC TAT CTG GGC CCC   2331
      L   D   S   R   P   G   V   L   K   E   P   K   L   M   G   A   I   S   F   F    797
     TTG GAC TCC AGG CCC GGA GTG CTG AAG GAG CCC AAA CTG ATG GGT GCT ATC TCC TTC TTC   2391
      I   F   F   F   T   L   L   V   L   A   R   Q   N   E   Y   Y   C   R   L   D    817
```

FIG. 1B.

```
ATC TTC TTC TTC ACC CTC CTT GTC CTG GCT CGC CAG AAT GAG TAC TAC TGC CGC CTG GAG    2451
 I   F   F   F   T   L   L   V   L   A   R   Q   N   E   Y   Y   C   R   L   E     837
TTC CTG TGG AAG AAG AAG CTG AGG CAG GAG AGG GAG GAG ACA GAG ACG ATG GAG AAC CTG    2511
 F   L   W   K   K   K   L   R   Q   E   R   E   E   T   E   T   M   E   N   L     857
ACT CGG CTG CTC TTG GAG AAC GTG CTC CCT GCA CAC GTG GCC CCC CAG TTC ATT GGC CAG    2571
 T   R   L   L   L   E   N   V   L   P   A   H   V   A   P   Q   F   I   G   Q     877
AAC CGG CGC AAC GAG GAT CTC TAC CAC CAG TCC TAT GAA TGC GTT TGT GTC CTC TTC GCC    2631
 N   R   R   N   E   D   L   Y   H   Q   S   Y   E   C   V   C   V   L   F   A     897
TCA GTC CCA GAC TTC AAG GAG TTC TAC TCT GAA TCC AAC ATC AAT CAT GAG GGC CTA GAG    2691
 S   V   P   D   F   K   E   F   Y   S   E   S   N   I   N   H   E   G   L   E     917
TGT CTG AGG CTG CTC AAT GAG ATA ATT GCT GAT TTT GAT GAG CTG CTC TCC AAG CCC AAG    2751
 C   L   R   L   L   N   E   I   I   A   D   F   D   E   L   L   S   K   P   K     937
TTC AGT GGG GTG GAG AAG ATC AAG ACC ATC GGC AGC ACC TAC ATG GCA GCC ACA GGC TTA    2811
 F   S   G   V   E   K   I   K   T   I   G   S   T   Y   M   A   A   T   G   L     957
AAT GCC ACC TCT GGA CAG GAT GCA CAA CAG GAT GCT GAA CGG AGC TGC AGC CAC CTT GGC    2871
 N   A   T   S   G   Q   D   A   Q   Q   D   A   E   R   S   C   S   H   L   G     977
ACT ATG GTG GAA TTT GCC GTG GCC CTG GGG TCT AAG CTG GAC GTC ATC AAC AAG CAT TCA    2931
 T   M   V   E   F   A   V   A   L   G   S   K   L   D   V   I   N   K   H   S     997
TTC AAC AAC TTC CGC CTG CGA GTG GGG TTG AAC CAT GGA CCC GTA GTA GCT GGA GTT ATT    2991
 F   N   N   F   R   L   R   V   G   L   N   H   G   P   V   V   A   G   V   I    1017
GGG GCC CAG AAG CCG CAA TAT GAC ATT TGG GGC AAC ACA GTG AAC GTG GCC AGC CGC ATG    3051
 G   A   Q   K   P   Q   Y   D   I   W   G   N   T   V   N   V   A   S   R   M    1037
GAG AGT ACA GGA GTC CTT GGC AAA ATC CAA GTG ACT GAG GAG ACA GCA TGG GCC CTA CAG    3111
 E   S   T   G   V   L   G   K   I   Q   V   T   E   E   T   A   W   A   L   Q    1057
TCC CTG GGC TAC ACC TGC TAC AGC CGG GGT GTC ATC AAG GTG AAA GGC AAA GGG CAG CTC    3171
 S   L   G   Y   T   C   Y   S   R   G   V   I   K   V   K   G   K   G   Q   L    1077
TGC ACC TAC TTC CTG AAC ACA GAC TTG ACA CGA ACT GGA CCT CCT TCA GCT ACC TA GGC    3231
 C   T   Y   F   L   N   T   D   L   T   R   T   G   P   P   S   A   T   L   G
 *                                                                                 1078
TGA                                                                                3234
GATTGCACTCGCCTTCTAAGAACCTCAATAAAGAGACT
```

FIG. 1C.

Prosite Pattern Matches for 21529
Prosite version: Release 12.2 of February 1995

>PS00001/PDOC00001/ASN_GLYCOSYLATION N-glycosylation site.

Query: 697    NVSS    700
Query: 704    NLSW    707
Query: 836    NLTR    839
Query: 938    NATS    941

>PS00005/PDOC00005/PKC_PHOSPHO_SITE Protein kinase C phosphorylation site.

Query: 6      SPR     8
Query: 51     SGR     53
Query: 202    TFR     204
Query: 212    SRR     214
Query: 218    TEK     220
Query: 290    SPK     292
Query: 526    TPR     528
Query: 550    SQK     552
Query: 606    TNR     608

>PS00006/PDOC00006/CK2_PHOSPHO_SITE Casein kinase II phosphorylation site.

Query: 51     SGRE    54
Query: 115    SAWD    118
Query: 202    TFRE    205
Query: 253    SRPE    256
Query: 290    SPKE    293
Query: 303    SLPD    336
Query: 359    TGVD    362
Query: 465    SSLE    468
Query: 495    SHGD    498
Query: 687    TSSD    690
Query: 878    SVPD    881
Query: 919    SGVE    922
Query: 941    SGQD    944
Query: 958    TMVE    961
Query: 968    SKLD    971
Query: 1015   SRME    1018

>PS00007/PDOC00007/TYR_PHOSPHO_SITE Tyrosine kinase phosphorylation site.

Query: 318    KILGDCYY    325
Query: 437    RELGEPTY    444
Query: 570    KEMEKEY     576
Query: 859    RRNEDLY     865

FIG. 4A.

>PS00008/PDOC00008/MYRISTYL N-myristoylation site.

| Query: | 35   | GIVLCA | 40   |
|--------|------|--------|------|
| Query: | 111  | GGVVSA | 116  |
| Query: | 137  | GMRDAA | 142  |
| Query: | 145  | GLASSL | 150  |
| Query: | 184  | GNVAGV | 189  |
| Query: | 329  | GLPLSL | 334  |
| Query: | 345  | GLDMCR | 350  |
| Query: | 360  | GVDINM | 365  |
| Query: | 368  | GVHSGS | 373  |
| Query: | 402  | GGVPGR | 407  |
| Query: | 412  | GATLAL | 417  |
| Query: | 458  | GTAGGL | 463  |
| Query: | 654  | GLVATR | 659  |
| Query: | 661  | GLRIAL | 666  |
| Query: | 936  | GLNATS | 941  |
| Query: | 995  | GVIGAQ | 1000 |
| Query: | 1008 | GNTVNV | 1013 |
| Query: | 1055 | GQLCTY | 1060 |

>PS00013/PDOC00013/PROKAR_LIPOPROTEIN Prokaryotic membrane lipoprotein lipid attachment site.
```
Non-eukaryotic pattern
RU   Additional rules:
RU   (1) The cysteine must be between positions 15 and 35 of the sequence in
RU   consideration.
RU   (2) There must be at least one charged residue (Lys or Arg) in the first
RU   seven residues of the sequence.
```

Query:  745    LLLLLWLAASC    755

>PS00029/PDOC00029/LEUCINE_ZIPPER leucine zipper pattern.

Query:  55    LTSDPSFLTTVLCALGGFSLLL  76

>PS00452/PDOC00425/GUANYLATE_CYCLASES Guanylate cyclases signature.

Query:  377    GVIGLQKWQYDVWSHDVTLANHME    400
Query:  995    GVIGAQKPQYDIWGNTVNVASRME    1018

FIG. 4B.

Bold letters indicate forskolin binding residues
Bold letters with an asterisk underneath indicate ATP-binding residues

```
      CTTCTACAATCGGGGTTTGAGGAAGAAGAAGAAAAGGACTGAAGGATCCCTTCATCGCCA
  1   ---------+---------+---------+---------+---------+---------+  60
      GCTGGAAGCGGGCTTGGGAGCCCGCAAGGAGGGCCTGAAAAAGAAGACGGGATTGCCACA
 61   ---------+---------+---------+---------+---------+---------+ 120
      AGGTTGGGGGCGCGGGGTGGTACGGCTTTGAGCGGGTGAGAAAAGCTCAGGTGGGGCCCG
121   ---------+---------+---------+---------+---------+---------+ 180
      CCGGGCCGAAGGAGGTAACCCGGCGCCCGGCCCTAGCCAGCCCCGGGGCTCGGGGCTGGG
181   ---------+---------+---------+---------+---------+---------+ 240
      GAGATCATGGCCCGCCTCTTCAGCCCCCGGCCGCCCCCCAGCGAAGACCTCTTCTACGAG
241   ---------+---------+---------+---------+---------+---------+ 300
               M  A  R  L  F  S  P  R  P  P  P  S  E  D  L  F  Y  E
      ACCTACTACAGCCTGAGCCAGCAGTACCCGCTGCTGCTGCTGCTGCTGGGGATCGTGCTC
301   ---------+---------+---------+---------+---------+---------+ 360
       T  Y  Y  S  L  S  Q  Q  Y  P  L  L  L  L  L  L  G  I  V  L
                                     ‾‾‾‾‾‾‾‾‾‾‾‾‾‾‾‾‾‾‾‾‾‾‾‾‾‾‾‾
                                                 TM-I
      TGTGCGCTCGCGGCGCTGCTCGCAGTGGCCTGGGCCAGCGGCAGGGAGCTGACCTCAGAC
361   ---------+---------+---------+---------+---------+---------+ 420
       C  A  L  A  A  L  L  A  V  A  W  A  S  G  R  E  L  T  S  D
      ‾‾‾‾‾‾‾‾‾‾‾‾‾‾‾‾‾‾‾‾‾‾‾‾‾‾‾‾‾‾‾‾‾                ‾‾‾‾‾‾‾‾‾‾‾
              TM-I
      CCGAGCTTCCTGACCACTGTGCTGTGCGCGCTGGGCGGCTTCTCGCTGCTGCTGGGCCTC
421   ---------+---------+---------+---------+---------+---------+ 480
       P  S  F  L  T  T  V  L  C  A  L  G  G  F  S  L  L  L  G  L
      ‾‾‾‾‾‾‾‾‾‾‾‾‾‾‾‾‾‾‾‾‾‾‾‾‾‾‾‾‾‾‾‾‾‾‾‾‾‾‾‾‾‾
           Leucine Zipper Domain              TM-II
      GCTTCCCGGGAGCAGCGACTGCAGCGCTGGACGCGTCCCCTGTCCGGCTTGGTATGGGTC
481   ---------+---------+---------+---------+---------+---------+ 540
       A  S  R  E  Q  R  L  Q  R  W  T  R  P  L  S  G  L  V  W  V
       ‾‾                                            ‾‾‾‾‾‾‾‾‾‾‾
      GCGCTGCTAGCGCTAGGCCACGCCTTCCTGTTCACCGGGGGCGTGGTGAGCGCCTGGGAC
541   ---------+---------+---------+---------+---------+---------+ 600
       A  L  L  A  L  G  H  A  F  L  F  T  G  G  V  V  S  A  W  D
       ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                        TM-III
      CAGGTGTCCTATTTTCTCTTCGTCATCTTCACGGCGTATGCCATGCTGCCCTTGGGCATG
601   ---------+---------+---------+---------+---------+---------+ 660
       Q  V  S  Y  F  L  F  V  I  F  T  A  Y  A  M  L  P  L  G  M
          ‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                              TM-IV
```

FIG. 6A.

```
     CGGGACGCCGCCGTCGCGGGCCTCGCCTCCTCACTCTCGCATCTGCTGGTCCTCGGGCTG
661  ------------+---------+---------+---------+---------+---------+ 720
     R  D  A  A  V  A  G  L  A  S  S  L  S  H  L  L  V  L  G  L
              ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                   TM-V
     TATCTTGGGCCACAGCCGGACTCACGGCCTGCACTGCTGCCGCAGTTGGCAGCAAACGCA
721  ------------+---------+---------+---------+---------+---------+ 780
     Y  L  G  P  Q  P  D  S  R  P  A  L  L  P  Q  L  A  A  N  A
     ‾‾‾‾‾‾‾‾‾‾‾‾                    ‾‾‾‾‾‾‾‾‾‾‾‾‾‾‾‾‾‾‾‾‾‾‾‾‾‾‾‾‾
                                              TM-VI
     GTGCTGTTCCTGTGCGGGAACGTGGCAGGAGTGTACCACAAGGCGCTGATGGAGCGCGCC
781  ------------+---------+---------+---------+---------+---------+ 840
     V  L  F  L  C  G  N  V  A  G  V  Y │ H  K  A  L  M  E  R  A
     ‾‾‾‾‾‾‾‾‾‾‾‾‾‾‾‾‾‾‾‾‾‾‾‾‾‾‾‾‾‾‾‾‾‾‾   └─► Cytoplasmic domain
     CTGCGGGCCACGTTCCGGGAGGCACTCAGCTCCCTGCACTCACGCCGGCGGCTGGACACC
841  ------------+---------+---------+---------+---------+---------+ 900
     L  R  A  T  F  R  E  A  L  S  S  L  H  S  R  R  R  L  D  T GAGAAGAAGCACCAAGAACACCTTCTCTTGTCCATCCTTCCTGCCTACCTGGCCCGAGAG
901  ------------+---------+---------+---------+---------+---------+ 960
     E  K  K  H  Q  E  H  L  L  L  S  I  L  P  A  Y  L  A  R  E ATGAAGGCAGAGATCATGGCACGGCTGCAGGCAGGACAGGGGGTCACGGCCAGAGAGCACT
961  ------------+---------+---------+---------+---------+---------+ 1020
     M  K  A  E  I  M  A  R  L  Q  A  G  Q  G  S  R  P  E  S  T AACAATTTCCACAGCCTCTATGTCAAGAGGCACCAGGGAGTCAGCGTGCTGTATGCTGAC
1021 ------------+---------+---------+---------+---------+---------+ 1080
     N  N  F  H  S  L  Y  V  K  R  H  Q  G  V  S  V  L  Y  A  D ATCGTGGGCTTCACGCGGCTGGCCAGCGAGTGTTCCCCTAAGGAGCTGGTGCTCATGCTC
1081 ------------+---------+---------+---------+---------+---------+ 1140
     I  V  G  F  T  R  L  A  S  E  C  S  P  K  E  L  V  L  M  L AATGAGCTCTTTGGCAAGTTCGACCAGATTGCCAAGGAGCATGAATGCATGCGGATCAAG
1141 ------------+---------+---------+---------+---------+---------+ 1200
     N  E  L  F  G  K  F  D  Q  I  A  K  E  H  E  C  M  R  I  K ATCCTGGGGGACTGTTACTACTGTGTCTCTGGGCTGCCACTCTCACTGCCAGACCATGCC
1201 ------------+---------+---------+---------+---------+---------+ 1260
     I  L  G  D  C  Y  Y  C  V  S  G  L  P  L  S  L  P  D  H  A
           ‾        ‾                       ‾‾‾‾‾‾‾‾‾‾‾‾‾‾‾‾‾‾‾‾‾‾‾
     ATCAACTGCGTGCGCATGGGCCTGGACATGTGCCGGGCCATCAGGAAACTGCGGGCAGCC
1261 ------------+---------+---------+---------+---------+---------+ 1320
     I  N  C  V  R  M  G  L  D  M  C  R  A  I  R  K  L  R  A  A
     ‾
     ACTGGCGTGGACATCAACATGCGTGTGGGCGTGCACTCAGGCAGCGTACTGTGTGGAGTC
1321 ------------+---------+---------+---------+---------+---------+ 1380
     T  G  V  D  I  N  M  R  V  G  V  H  S  G  S  V  L  C  G  V
                            *                                   ‾
              The above R involved in Ppi binding
     ATCGGGCTGCAGAAGTGGCAGTACGACGTTTGGTCACATGATGTCACACTGGCTAACCAC
1381 ------------+---------+---------+---------+---------+---------+ 1440
     I  G  L  Q  K  W  Q  Y  D  V  W  S  H  D  V  T  L  A  N  H
     ‾‾‾‾‾‾‾‾‾‾‾‾‾‾‾‾‾‾‾‾‾‾‾‾‾    ‾‾‾‾‾‾‾‾‾‾‾‾‾‾‾‾‾‾‾‾‾‾‾‾‾‾‾‾‾‾‾
```

FIG. 6B.

```
              ATGGAGGCAGGCGGTGTACCAGGGCGAGTGCACATCACAGGGGCTACCCTGGCCCTGCTG
     1441     ---------+---------+---------+---------+---------+---------+   1500
              M  E  A  G  G  V  P  G  R  V  H  I  T  G  A  T  L  A  L  L
                *
              The above E is involved in Mg+2 binding
              GCAGGGGCTTATGCTGTGGAGGACGCAGGCATGGAGCATCGGGACCCCTACCTTCGGGAG
     1501     ---------+---------+---------+---------+---------+---------+   1560
              A  G  A  Y  A  V  E  D  A  G  M  E  H  R  D  P  Y  L  R  E CTAGGGGAGCCTACCTATCTGGTCATCGATCCACGGGCAGAGGAGGAGGATGAGAAGGGC
     1561     ---------+---------+---------+---------+---------+---------+   1620
              L  G  E  P  T  Y  L  V  I  D  P  R  A  E  E  E  D  E  K  G ACTGCAGGAGGCTTGCTGTCCTCGCTTGAGGGCCTCAAGATGCGTCCATCACTGCTGATG
     1621     ---------+---------+---------+---------+---------+---------+   1680
              T  A  G  G  L  L  S  S  L  E  G  L  K  M  R  P  S  L  L  M ACCCGTTACCTGGAGTCCTGGGGGGCAGCCAAGCCTTTTGCCCACCTGAGCCACGGAGAC
     1681     ---------+---------+---------+---------+---------+---------+   1740
              T  R  Y  L  E  S  W  G  A  A  K  P  F  A  H  L  S  H  G  D AGCCCTGTGTCCACCTCCACCCCTCTCCCGGAGAAGACCCTGGCTTCCTTCAGCACCCAG
     1741     ---------+---------+---------+---------+---------+---------+   1800
              S  P  V  S  T  S  T  P  L  P  E  K  T  L  A  S  F  S  T  Q TGGAGCCTGGATCGGAGCCGTACCCCCCGGGGACTAGATGATGAACTGGACACCGGGGAT
     1801     ---------+---------+---------+---------+---------+---------+   1860
              W  S  L  D  R  S  R  T  P  R  G  L  D  D  E  L  D  T  G  D GCCAAGTTCTTCCAGGTCATTGAGCAGCTCAACTCGCAGAAACAGTGGAAGCAGTCGAAG
     1861     ---------+---------+---------+---------+---------+---------+   1920
              A  K  F  F  Q  V  I  E  Q  L  N  S  Q  K  Q  W  K  Q  S  K GACTTCAACCCACTGACACTGTACTTCAGAGAGAAGGAGATGGAGAAAGAGTACCGACTC
     1921     ---------+---------+---------+---------+---------+---------+   1980
              D  F  N  P  L  T  L  Y  F  R  E  K  E  M  E  K  E  Y  R  L TCTGCAATCCCCGCCTTCAAATACTATGAAGCCTGCACCTTCCTGGTTTTTCTCTCCAAC
     1981     ---------+---------+---------+---------+---------+---------+   2040
              S  A  I  P  A  F  K  Y  Y  E  A  C  T  F  L  V  F  L  S  N
                    Cytoplasmic      ←┘              TM-VII
              TTCATCATCCAGATGCTAGTGACAAACAGGCCCCCAGCTCTGGCCATCACGTATAGCATC
     2041     ---------+---------+---------+---------+---------+---------+   2100
              F  I  I  Q  M  L  V  T  N  R  P  P  A  L  A  I  T  Y  S  I
                                                        TM-VIII
              ACTTTCCTCCTCTTCCTCCTCATCCTTTTTGTCTGCTTCTCAGAGGACCTGATGAGGTGT
     2101     ---------+---------+---------+---------+---------+---------+   2160
              T  F  L  L  F  L  L  I  L  F  V  C  F  S  E  D  L  M  R  C

GTCCTGAAAGGCCCCAAGATGCTGCACTGGCTGCCTGCACTGTCTGGCCTGGTGGCCACA
```

CGACCAGGACTGAGAATAGCCTTGGGCACCGCCACCATCCTCCTTGTCTTTGCCATGGCC
2221 ----------+---------+---------+---------+---------+---------+ 2280
     R  P  G  L  R  I  A  L  G  T  A  T  I  L  L  V  F  A  M  A
                     ────────────TM-IX─────────────────────

ATTACCAGCCTGTTCTTCTTCCCAACATCATCAGACTGCCCTTTCCAAGCTCCCAATGTG
2281 ----------+---------+---------+---------+---------+---------+ 2340
     I  T  S  L  F  F  F  P  T  S  S  D  C  P  F  Q  A  P  N  V
     ──────────────────                            Extracellular TCCTCCATGATTTCCAACCTCTCCTGGGAGCTCCCTGGGTCTCTGCCTCTCATCAGTGTC
2341 ----------+---------+---------+---------+---------+---------+ 2400
     S  S  M  I  S  N  L  W  E  L  P  G  S  L  P  L  I  S  V
                                       ────────TM-X───────

CCATACTCCATGCACTGCTGCACGCTGGGCTTCCTCTCCTGCTCCCTCTTTCTGCACATG
2401 ----------+---------+---------+---------+---------+---------+ 2460
     P  Y  S  M  H  C  C  T  L  G  F  L  S  C  S  L  F  L  H  M
     ────────────────────────────────────────────────────────────

AGCTTCGAGCTGAAGCTGCTGCTGCTGCTCCTGCTGTGGCTGGCGGCATCCTGCTCCCTCTTC
2461 ----------+---------+---------+---------+---------+---------+ 2520
     S  F  E  L  K  L  L  L  L  L  L  W  L  A  A  S  C  S  L  F
                       ─────────────TM-XI─────────────────

CTGCACTCCCATGCCTGGCTGTCGGAATGCCTCATCGTCCGCCTCTATCTGGGCCCCTTG
2521 ----------+---------+---------+---------+---------+---------+ 2580
     L  H  S  H  A  W  L  S  E  C  L  I  V  R  L  Y  L  G  P  L
     ─────────────

GACTCCAGGCCCGGAGTGCTGAAGGAGCCCAAACTGATGGGTGCTATCTCCTTCTTCATC
2581 ----------+---------+---------+---------+---------+---------+ 2640
     D  S  R  P  G  V  L  K  E  P  K  L  M  G  A  I  S  F  F  I
                                      ─────────TM-XII──────

TTCTTCTTCACCCTCCTTGTCCTGGCTCGCCAGAATGAGTACTACTGCCGCCTGGACTTC
2641 ----------+---------+---------+---------+---------+---------+ 2700
     F  F  F  T  L  L  V  L  A  R  Q  N  E  Y  Y  C  R  L  D  F
     ──────────────────── └→  Cytoplasmic CTGTGGAAGAAGAAGCTGAGGCAGGAGAGGGAGGAGACAGAGACGATGGAGAACCTGACT
2701 ----------+---------+---------+---------+---------+---------+ 2760
     L  W  K  K  K  L  R  Q  E  R  E  E  T  E  T  M  E  N  L  T CGGCTGCTCTTGGAGAACGTGCTCCCTGCACACGTGGCCCCCCAGTTCATTGGCCAGAAC
2761 ----------+---------+---------+---------+---------+---------+ 2820
     R  L  L  L  E  N  V  L  P  A  H  V  A  P  Q  F  I  G  Q  N CGGCGCAACGAGGATCTCTACCACCAGTCCTATGAATGCGTTTGTGTCCTCTTCGCCTCA
2821 ----------+---------+---------+---------+---------+---------+ 2880
     R  R  N  E  D  L  Y  H  Q  S  Y  E  C  V  C  V  L  F  A  S GTCCCAGACTTCAAGGAGTTCTACTCTGAATCCAACATCAATCATGAGGGCCTAGAGTGT
2881 ----------+---------+---------+---------+---------+---------+ 2940
     V  P  D  F  K  E  F  Y  S  E  S  N  I  N  H  E  G  L  E  C
```

FIG. 6D.

```
      CTGAGGCTGCTCAATGAGATAATTGCTGATTTTGATGAGCTGCTCTCCAAGCCCAAGTTC
2941  ---------+---------+---------+---------+---------+---------+  3000
      L  R  L  L  N  E  I  I  A  D  F  D  E  L  L  S  K  P  K  F

AGTGGGGTGGAGAAGATCAAGACCATCGGCAGCACCTACATGGCAGCCACAGGCTTAAT
3001  ---------+---------+---------+---------+---------+---------+  3060
      S  G  V  E  K  I  K  T  I  G  S  T  Y  M  A  A  T  G  L  N

GCCACCTCTGGACAGGATGCACAACAGGATGCTGAACGGAGCTGCAGCCACCTTGGCACT
3061  ---------+---------+---------+---------+---------+---------+  3120
      A  T  S  G  Q  D  A  Q  Q  D  A  E  R  S  C  S  H  L  G  T

ATGGTGGAATTTGCCGTGGCCCTGGGGTCTAAGCTGGACGTCATCAACAAGCATTCATTC
3121  ---------+---------+---------+---------+---------+---------+  3180
      M  V  E  F  A  V  A  L  G  S  K  L  D  V  I  N  K  H  S  F

AACAACTTCCGCCTGCGAGTGGGGTTGAACCATGGACCCGTAGTAGCTGGAGTTATTGGG
3181  ---------+---------+---------+---------+---------+---------+  3240
      N  N  F  R  L  R  V  G  L  N  H  G  P  V  V  A  G  V  I  G
      R above, has been* shown to bind PPi GCCCAGAAGCCGCAATATGACATTTGGGGCAACACAGTGAACGTGGCCAGCCGCATGGAG
3241  ---------+---------+---------+---------+---------+---------+  3300
      A  Q  K  P  Q  Y  D  I  W  G  N  T  V  N  V  A  S  R  M  E
                         Cyclase (C2) Domain  *           *    *

AGTACAGGAGTCCTTGGCAAAATCCAAGTGACTGAGGAGACAGCATGGGCCCTACAGTCC
3301  ---------+---------+---------+---------+---------+---------+  3360
      S  T  G  V  L  G  K  I  Q  V  T  E  E  T  A  W  A  L  Q  S

CTGGGCTACACCTGCTACAGCCGGGGTGTCATCAAGGTGAAAGGCAAAGGGCAGCTCTGC
3361  ---------+---------+---------+---------+---------+---------+  3420
      L  G  Y  T  C  Y  S  R  G  V  I  K  V  K  G  K  G  Q  L  C
                                                 *

ACCTACTTCCTGAACACAGACTTGACACGAACTGGACCTCCTTCAGCTACCCTAGGCTGA
3421  ---------+---------+---------+---------+---------+---------+  3480
      T  Y  F  L  N  T  D  L  T  R  T  G  P  P  S  A  T  L  G  *

GATTGCACTCGCCTTCTAAGAACCTCAATAAAGAGACT
3481  ---------+---------+---------+------  3518
```

FIG. 6E.

| Summary of Taqman Results: Oncology Panel | | |
|---|---|---|
| Tissue | Mean | Relative Expression |
| Breast Normal | 51.6 ± 85.7 | 1.0 |
| Breast Tumor | 72.4 ± 38.3 | 1.4 |
| Lung Normal | 19.8 ± 13.2 | 1.0 |
| Lung Tumor | 11.0 ± 10.7 | 0.6 |
| Colon Normal | 36.1 ± 31.4 | 1.0 |
| Colon Tumor | 11.8 ± 8.3 | 0.3 |
| Liver Normal | 4.6 ± 1.7 | 1.0 |
| Liver Metastases | 13.0 ± 3.8 | 2.8 |

FIG. 9.

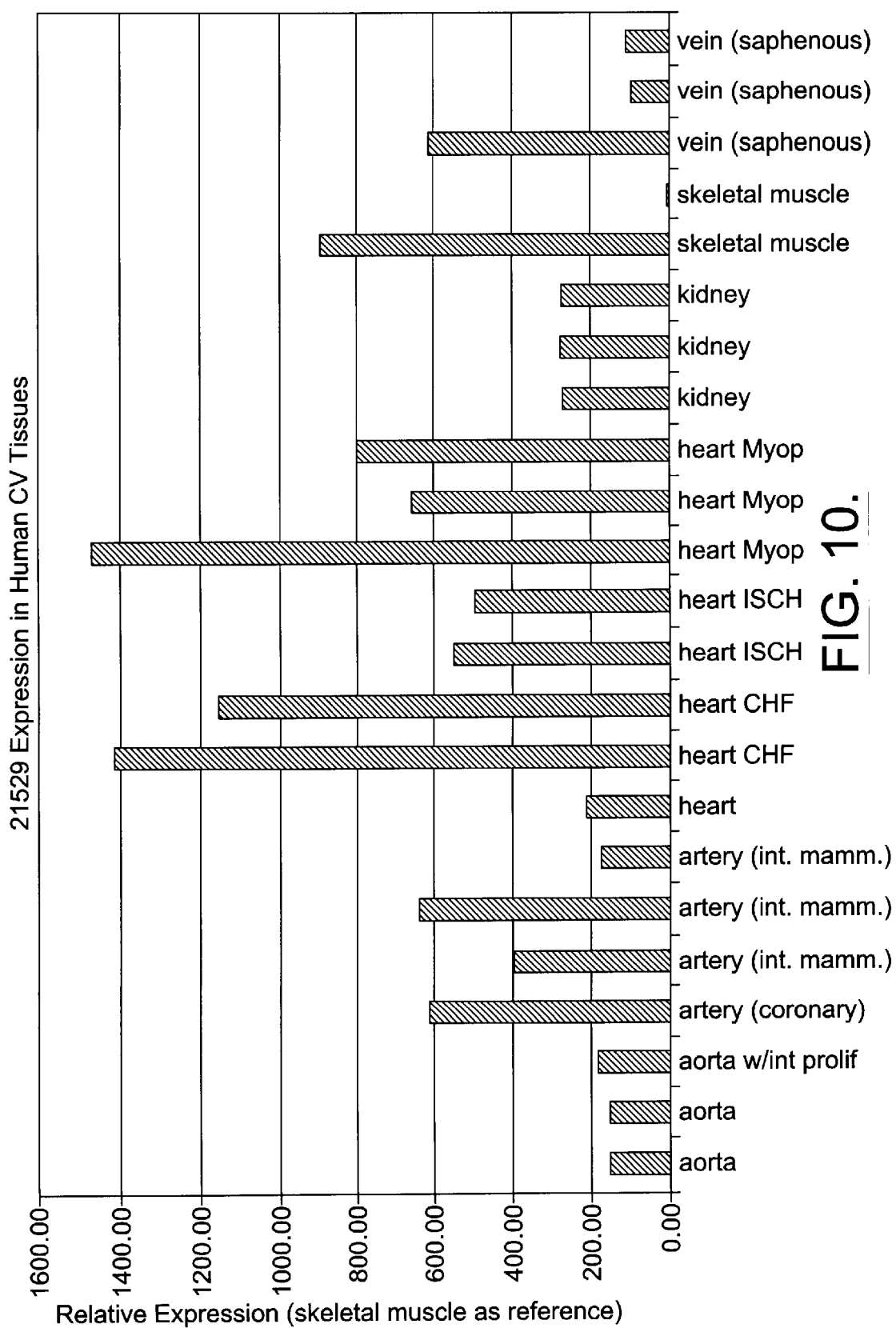

21529, A NOVEL ADENYLATE CYCLASE

CROSS-REFERENCE TO RELATED APPLICATIONS

This application is a divisional of U.S. application Ser. No. 09/412,210, filed Oct. 5, 1999, now U.S. Pat. No. 6,403,358, which is hereby incorporated in its entirety by reference herein.

FIELD OF THE INVENTION

The invention relates to novel adenylate cyclase nucleic acid sequences and proteins. Also provided are vectors, host cells, and recombinant methods for making and using the novel molecules.

BACKGROUND OF THE INVENTION

Adenylate cyclase is a membrane-bound enzyme that acts as an effector protein in a receptor-effector system referred to as the cAMP signal transduction pathway. As such, it plays a key intermediate role in the conversion of extracellular signals, perceived by various receptors following binding of a particular ligand, into intracellular signals that, in turn, generate specific cellular responses.

A variety of hormones, neurotransmitters, and olfactants regulate the synthesis of cAMP by adenylate cyclases. In most tissues, regulation of cAMP synthesis is accomplished through three plasma membrane-associated components: G-protein-coupled receptors (GPCRs), which interact with regulatory hormones and neurotransmitters; heterotrimeric G proteins that either stimulate or inhibit the catalytic subunit of adenylate cyclase in response to interaction of ligands with appropriate GPCRs; and the catalytic entity, adenylate cyclase. Each G protein contains a guanine nucleotide-binding alpha subunit and a complex of tightly associated β- and γ-subunits. When a G protein is activated following binding of a ligand to a GPCR, GDP is released from the α-subunit in exchange for GTP. Binding of the GTP results in conformational changes that yield dissociation of the GTP-bound α-subunit from the β-γ-subunit complex. The resulting macromolecular complexes regulate catalytic activity of adenylate cyclase. Where the receptor is a stimulatory receptor ($R_s$), interaction with a stimulatory G-protein, termed $G_s$, results in activation of the adenylate cyclase catalytic subunit by the GTP-bound form of the $G_s$ α-subunit. In contrast, where the receptor is an inhibitory receptor ($R_i$), interaction with an inhibitory G-protein (one of several known $G_i$s) results in inhibition of the adenylate cyclase catalytic subunit by the GTP-bound form of the $G_i$ α-subunit. In addition, the G-protein β-γ-subunit complex may interact with and influence adenylate cyclase activity independent of or in parallel with the GTP-bound α-subunit, depending upon the adenylate cyclase isoform involved. See Taussig and Gilman (1995) *J. Biol. Chem.* 6:1–4; Hardman et al., eds. (1996) *Goodman and Gilman's Pharmacological Basis of Therapeutics* (McGraw-Hill Company, New York, N.Y.).

When activated, the catalytic subunit of adenylate cyclase converts intracellular ATP into cAMP. This second messenger then activates protein kinases, particularly protein kinase A. Activation of this protein kinase causes the phosphorylation of downstream target proteins involved in a number of metabolic pathways, thus initiating a signal transduction cascade.

The extent to which adenylate cyclase converts ATP to cAMP is highly dependent on the state of phosphorylation of the various components of the hormone-sensitive adenylate cyclase system. For example, stimulatory and inhibitory receptors are desensitized and down-regulated following phosphorylation by various kinases, particularly cAMP-dependent protein kinases, protein kinase C, and other receptor-specific kinases that preferentially use agonist-bound forms of receptors as substrates. In this manner, tight regulation of the cellular cAMP concentration, and hence regulation of the cAMP signal transduction pathway, is achieved (Taussig and Gilman (1995) *J. Biol. Chem.* 270:1–4).

Adenylate cyclase activation may also occur through increased intracellular calcium concentration, especially in nervous system and cardiovascular tissues. After depolarization, the influx of calcium elicits the activation of calmodulin, an intracellular calcium-binding protein. In the cardiovascular system, this effect gives rise to the contraction of the blood vessels or cardiac myocytes. The activated calmodulin has been shown to bind and activate some isoforms of adenylate cyclase.

Several novel isoforms of mammalian adenylate cyclase have been identified through molecular cloning. Type I adenylate cyclase (CYA1) is primarily localized in brain tissues (see Krupinski et al (1989) *Science* 244:1558–1564; Gilman (1987) *Ann. Rev. Biochem.* 56:615–649, citing Salter et at. (1981) *J. Biol. Chem.* 256:9830–9833; Andreasen et al. (1983) *Biochemistry* 22:2757–2762; and Smigel et al (1986) *J. Biol Chem.* 261:1976–1982 for bovine CYA1; and Villacres et al. (1993) *Genomics* 16:473–478 for human CYA1). The type II adenylate cyclase (CYA2) is localized in brain and lung tissues (see Feinstein et al. (1991) *Proc. Natl. Acad. Sci. USA* 88:10173–10177 for rat CYA2; and Stengel et al. (1992) *Hum. Genet.* 90:126–130 for human CYA2). Type III adenylate cyclase (CYA3) is primarily localized in olfactory neuroepithelium and is thought to mediate olfactory receptor responses (Bakalyar and Reed (1990) *Science* 250:1403–1406; Glatt and Snyder (1993) *Nature* 361:536–538; and Xia (1992) *Neurosci. Lett.* 144:169–173). Type IV adenylate cyclase (CYA4) most resembles type II, but is expressed in a variety of peripheral tissues and in the central nervous system (Gao and Gilman (1991) *Proc. Natl. Acad. Sci. USA* 88:10178–10182, for rat CYA4). Type V adenylate cyclase (CYA5) (Ishikawa et al. (1992) *J. Biol. Chem.* 267:13553–13557; Premont et al. (1992) *Proc. Natl. Acad. Sci. USA* 89:9809–9813; and Glatt and Snyder (1993) *Nature* 361:536–538; Krupinski et al. (1992) *J. Biol. Chem.* 267:24858–24862) and type VI adenylate cyclase (CYA6) (Premont et al. (1992) *Proc. Natl. Acad. Sci. USA* 89:9808–9813; Yoshimura and Cooper (1992) *Proc. Natl. Acad. Sci. USA* 89:6716–6720; Katsushika et al. (1992) *Proc. Natl. Acad. Sci. USA* 89:8774–8778; and Krupinski et al. (1992) *J. Biol. Chem.* 267:24858–24862) both exhibit a widely distributed expression pattern, with type V having high expression in heart and striatum, and type VI having high expression in heart and brain. Type VII adenylate cyclase (CYA7) is widely distributed, though may be absent from brain tissues (Krupinski et al (1992) *J. Biol. Chem.* 267:24858–24862). Type VII adenylate cyclase (CYA8) is abundant in brain tissues (Krupinski et al. (1992) *J. Biol. Chem.* 267:24858–24862; and Parma et al. (1991) *Biochem. Biophys. Res. Commun.* 179:455–462). Type IX adenylate cyclase (CYA9) is widely expressed, at high levels in skeletal muscle and brain (Premont et al. (1996) *J. Biol. Chem.* 271:13900–13907).

The different isoforms of adenylate cyclase exhibit unique patterns of regulatory responses (see Sunahara et al. (1996) *Annu. Tev. Pharmacol. Toxicol* 36:461–480). For example, all of these isoforms are activated by the α-subunit of a particular G protein, termed $G_s$, which couples the stimulatory action of the ligand-bound receptor to activation of adenylate cyclase. The adenylate cyclases designated type I, III, and VIII are also stimulated by $Ca^{2+}$/calmodulin in vitro, while type II, IV, V, VI, VII, and IX are not. Type I is inhibited by G protein β-γ-subunit complex, independently of $G_s$ activation, while Type II is highly stimulated by G protein β-γ-subunit complex when simultaneously activated by Gs alpha subunit. Type III, in contrast, is not affected by G protein β-γ-subunit complex. Type V and type VI are both are inhibited by low levels of $Ca^{2+}$, but appear to be unaffected by G protein β-γ-subunit complex. Type IX is unique in that it is stimulated by $Mg^{2+}$, but is not affected by G protein β-γ-subunit complex.

The genes for these adenylate cyclases all encode proteins having molecular weights of approximately 120,000 and which range from 1064 to 1353 amino acid residues. These proteins are predicted to have a short cytoplasmic amino terminus followed by a first motif consisting of six transmembrane spans and a cytoplasmic (domain $C_1$), and then a second motif, also consisting of six transmembrane spans and a second cytoplasmic domain (domain $C_2$). The two cytoplasmic domains are approximately 40 kDa each and contain a region of homology (designated $C_{1a}$ and $C_{2a}$) with each other and with the catalytic domains of membrane-bound guanylate cyclases. Based on this similarity, these domains are considered to be nucleotide binding domains, and together have been shown to be sufficient to confer enzymatic activity (Tang and Gilman (1995) *Science* 268:1769–1772).

Alterations in the cAMP signal transduction pathway have been associated with diseases such as asthma, cancer, inflammation, hypertension, atherosclerosis, heart failure. Antihypertensive drug therapy involves modulation of adenylate cyclase levels (Marcil et al. (1996) *Hypertension* 28:83–90). In addition, studies of heart in human and animal models indicate that adenylate cyclase has a function in cardiomyopathy (Michael et al. (1995) *Hypertension* 25:962–970, Roth et al. (1999) *Circulation* 99:3099–3102), ischemia (Sandhu et al. (1996) *Circulation Research* 78:137–147), myocardial infarction (Espinasse et al. (1999) *Cardiovascular Research* 42:87–98) and congestive heart failure (Kawahira et al. (1998) *Circulation* 98:262–267, Panza et al. (1995) *Circulation* 91:1732–1738). The enzyme is also related to some mental disorders. Studies of learning and memory in animal models indicate a likely role for calmodulin-activated adenylate cyclases in conditioning (Abrams and Kandel (1988) *Trends Neurosci.* 11:128–135), learning (Livingstone et al. (1984) *Cell* 37:205–215), and long term potentiation (Frey et al. (1993) *Science* 260:161–1664). Furthermore, the cAMP signaling pathway plays an important role in cardiovascular physiology. For instance, cAMP activates protein kinase A (PKA). The activated subunits of PKA initiate a series of enzymatic reactions that ultimately activate multiple proteins that regulate both the rate and force of cardiac contraction.

Given the key role of adenylate cyclase in cAMP production, novel adenylate kinase molecules for the modulation of the cAMP signal transduction pathway are needed.

SUMMARY OF THE INVENTION

Isolated nucleic acid molecules corresponding to adenylate cyclase nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequences encoding the DNA sequence deposited in a bacterial host with the Patent Depository of the American Type Culture Collection (ATCC) as Patent Deposit Number PTA-1661. Further provided are adenylate cyclase polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The adenylate cyclase molecules of the present invention are useful for modulating cellular growth and/or cellular metabolic pathways, particularly for regulating the cAMP signal transduction pathway and phosphorylation of proteins via cAMP-dependent protein kinases involved in cellular growth and metabolism. Accordingly, in one aspect, this invention provides isolated nucleic acid molecules encoding adenylate cyclase proteins or biologically active portions thereof, as well as nucleic acid fragments suitable as primers or hybridization probes for the detection of adenylate cyclase-encoding nucleic acids.

Another aspect of this invention features isolated or recombinant adenylate cyclase proteins and polypeptides. Preferred adenylate cyclase proteins and polypeptides possess at least one biological activity possessed by naturally occurring adenylate cyclase proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the adenylate cyclase polypeptides and fragments are provided. Such antibodies are useful in detecting the adenylate cyclase polypeptides as well as in regulating the T-cell immune response and cellular activity, particularly growth and proliferation.

In another aspect, the present invention provides a method for detecting the presence of adenylate cyclase activity or expression in a biological sample by contacting the biological sample with an agent capable of detecting an indicator of adenylate cyclase activity such that the presence of adenylate cyclase activity is detected in the biological sample.

In yet another aspect, the invention provides a method for modulating adenylate cyclase activity comprising contacting a cell with an agent that modulates (inhibits or stimulates) adenylate cyclase activity or expression such that adenylate cyclase activity or expression in the cell is modulated. In one embodiment, the agent is an antibody that specifically binds to adenylate cyclase protein. In another embodiment, the agent modulates expression of adenylate cyclase protein by modulating transcription of an adenylate cyclase gene, splicing of an adenylate cyclase mRNA, or translation of an adenylate cyclase mRNA. In yet another embodiment, the agent is a nucleic acid molecule having a nucleotide sequence that is antisense to the coding strand of the adenylate cyclase mRNA or the adenylate cyclase gene.

In one embodiment, the methods of the present invention are used to treat a subject having a disorder characterized by aberrant adenylate cyclase protein activity or nucleic acid expression by administering an agent that is an adenylate cyclase modulator to the subject. In one embodiment, the adenylate cyclase modulator is an adenylate cyclase protein. In another embodiment, the adenylate cyclase modulator is an adenylate cyclase nucleic acid molecule. In other embodiments, the adenylate cyclase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding an adenylate cyclase protein; (2) misregulation of a gene encoding an adenylate cyclase protein; and (3) aberrant post-translational modification of an adenylate cyclase protein, wherein a wild-type form of the gene encodes a protein with an adenylate cyclase activity.

In another aspect, the invention provides a method for identifying a compound that binds to or modulates the activity of an adenylate cyclase protein. In general, such methods entail measuring a biological activity of an adenylate cyclase protein in the presence and absence of a test compound and identifying those compounds that alter the activity of the adenylate cyclase protein.

The invention also features methods for identifying a compound that modulates the expression of adenylate cyclase genes by measuring the expression of the adenylate cyclase sequences in the presence and absence of the compound.

Other features and advantages of the invention will be apparent from the following detailed description and claims.

BRIEF DESCRIPTION OF THE DRAWINGS

FIGS. 1(A–C) shows the 21529 nucleotide sequence (SEQ ID NO:2) and the deduced amino acid sequence (SEQ ID NO:1).

FIGS. 4(A–B) shows an analysis of the 21529 open reading frame (SEQ ID NO:1) for amino acids corresponding to specific functional sites and regions as discussed in detail herein below.

FIGS. 6(A–E) shows a linear map of the 21529 protein (SEQ ID NO:1), delineating forskolin binding residues, ATP-binding residues, amino acids involved in binding of forskolin-purine (the circled residues), the G-βγ binding domain (the double underlined residues), protein kinase C binding domain (the triple underlined residues), and single underlined regions indicating transmembrane domains.

FIG. 9 shows a summary of Taqman results for breast, lung, and colon tumors as well as colon metastases to the liver.

FIG. 10 shows expression of the 21529 gene in human cardiovascular tissues.

DETAILED DESCRIPTION OF THE INVENTION

The present invention is based, at least in part, on the identification of novel molecules, referred to herein as adenylate cyclase nucleic acid and polypeptide molecules, which play a key role in regulation of the cyclic AMP (cAMP) signal transduction pathway by virtue of their conversion of intracellular ATP into cAMP. In one embodiment, the adenylate cyclase molecules modulate the activity of one or more proteins involved in cellular metabolism associated with cell maintenance, growth, or differentiation, e.g., cardiac, epithelial, or neuronal cell maintenance, growth, or differentiation. In another embodiment, the adenylate cyclase molecules of the present invention are capable of modulating the phosphorylation state of one or more proteins involved in cellular metabolism associated with cell maintenance, growth, or differentiation, e.g., cardiac, epithelial, or neuronal cell maintenance, growth or differentiation, via their indirect effect on cAMP-dependent protein kinases, particularly protein kinase A, as described in, for example, Devlin (1997) *Textbook of Biochemistry with Clinical Correlations* (Wiley-Liss, Inc., New York, N.Y.). In addition, the receptors which trigger activity of the adenylate cyclases of the present invention are targets of drugs as described in Goodman and Gilman (1996), *The Pharmacological Basis of Therapeutics* ($9^{th}$ ed.) Hartman & Limbard Editors, the contents of which are incorporated herein by reference. Particularly, the adenylate cyclase molecules of the invention may modulate phosphorylation activity in tissues in which the polypeptides are highly expressed, including but not limited to skeletal muscle, heart, cervix, vein, brain, pancreas, breast, fetal kidney, fetal liver, and fetal heart.

Figure 8:
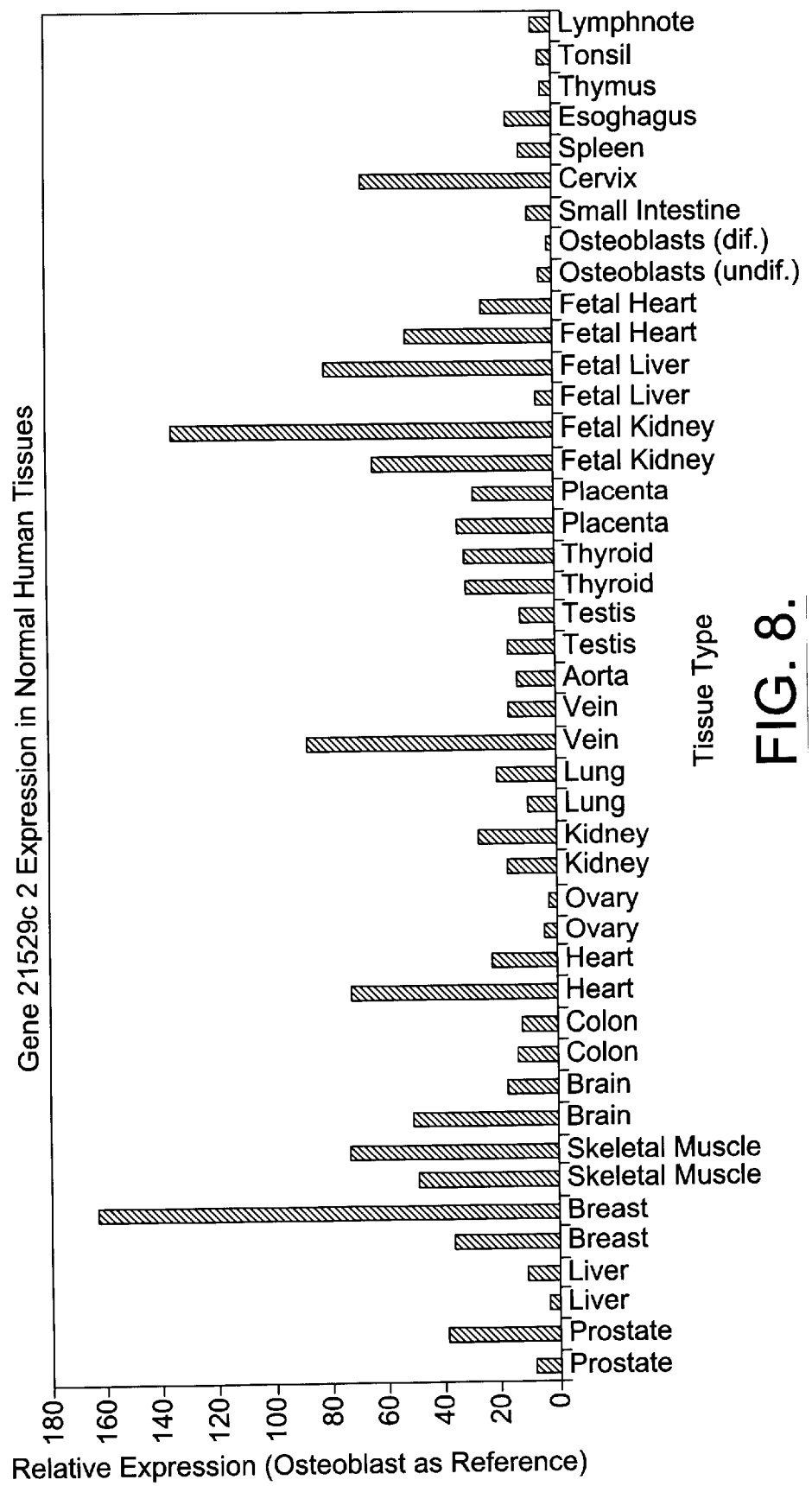
FIG. 8 shows expression of the 21529 gene in normal human tissues.

Furthermore, expression may be modulated in other tissues in which the polypeptides are expressed including, but not limited to, those shown in FIG. 8, which provides a profile of expression in normal human tissues. In addition, upregulation is observed in breast carcinoma. Therefore, modulation is particularly relevant in this disorder. Further, downregulation is shown in both lung and colon carcinoma. Therefore, modulation is also relevant in these tissues. In colonic liver metastases, however, there is significant upregulation. Accordingly, modulation is important in these tissues. Further, as shown in FIG. 10, expression occurs in cardiovascular tissues. These include, but are not limited to, aorta, aorta with intimal proliferation (atheroplaques), coronary artery, internal mammary artery, heart, especially heart derived from patients with congestive heart failure and heart tissue derived from myopathic patients, ischemic heart, and saphenous vein, (the chief superficial vein found in the human leg). Finally, as further discussed herein, the gene is expressed in hypertrophic cardiac myocytes from diseased subjects. Accordingly, modulation is particularly relevant in disorders that include but are not limited to congestive heart failure, ischemia, hypertension, myocardial infarction, atherosclerosis, cardiomyopathy, and other diseases of the cardiovascular system as disclosed herein.

In a preferred embodiment, the adenylate cyclase molecules of the invention are used to modulate the cyclic AMP (cAMP) signal transduction pathway. Cyclic AMP is a second messenger produced in response to ligand-induced stimulation of certain G-protein-coupled receptors (GPCR). In the cAMP signal transduction pathway, binding of a ligand to a GPCR leads to the activation of adenylate cyclase, which then catalyzes the synthesis of cAMP. The newly synthesized cAMP can in turn activate a cAMP-dependent protein kinase, such as protein kinase A. The activated cAMP-dependent kinases can, through a series of intermediate steps, regulate transcription factors and stimulate expression of target genes, as well as phosphorylate other downstream target proteins that are involved in a host of metabolic pathways. In addition, activated cAMP-dependent protein kinases can phosphorylate a voltage-gated potassium channel protein and lead to the inability of the potassium channel to open during an action potential. The inability of the potassium channel to open results in a decrease in the outward flow of potassium, which normally repolarizes the membrane of a neuron, leading to prolonged membrane depolarization.

Cyclic AMP also influences cardiovascular physiology. For instance, cAMP activates protein kinase A (PKA). The activated subunits of PKA initiate a series of enzymatic reactions that ultimately activate multiple proteins that regulate both the rate and force of cardiac contraction. For instance, phosphorylation of the L-type calcium channel enhances calcium entry into cardiocytes leading to increased contractility. Upon phosphorylation of phospholamban, the inhibition exerted by the non phosphorylated form of phospholamban on the sarcoplasmic reticulium calcium pump is removed, and its rate of calcium uptake increased, thereby leading to a more rapid decrease of the cytosolic calcium concentration during diastole. Dissociation of the troponin C-calcium complex is also enhanced when troponin I is phosphorylated which leads to an accelerated relaxation rate. Such events result in the enhancement of cardiac output. This process rapidly reverses when agonist occupancy of the receptor ceases, i.e. the reuptake of norepinephrine into presynaptic stores. For a review, see for example, Yoshihiro et al. (1997) *Circulation Research* 80:297–304 and Castellano et al. (1997) *Hypertension* 29:715–722.

As the enzyme that catalyzes conversion of intracellular ATP to cAMP, adenylate cyclase plays a central role in the regulation of cellular cAMP concentrations. Disruption or modulation of adenylate cyclase activity affects intracellular concentrations of cAMP, which can in turn modulate the cAMP signal transduction pathway.

Many cardiovascular patho-physiological conditions result from modulations in the cAMP signaling pathway. Therefore, changes in concentration and function of receptors, G-proteins, and adenylate cyclase may thus constitute fundamental defects underlying certain cardiac diseases.

Alterations that accompany physiological changes in cardiovascular function include, for example, transformations of the myocardial structure and function such as a transition of the myosin heavy chain isoform (Imumo et al. (1987) *J Clin Invest* 79:970–977), accumulation of alpha-skeletal muscle actin mRNA (Schwartz et al (1986) *Circ Res* 59:551–555) changes in troponin isoforms (Mayer et al. (1995) *Curr Opin Cardiol* 10:238–245) deterioration of Na+K+-ATPases (Charlemagne et al. (1986) *J Biol Chem* 261:185–189) and collagen remodeling of myocardium (Wever et al. (1988) *Circ Res* 62:757–763). Further changes in physiological cardiovascular function resulting from various forms of heart failure include alterations in arterial tone and reactivity and alterations in platelet function including aggregation, secretion, and clot formation and blood pressure elevation. (Marcil et al (1996) *Hypertension* 28:83–90).

Adenylate cyclase has been implicated in many cardiovascular diseases. For example, adenylate cyclase activity and its responsiveness to various hormones is altered in hypertensive patients. Aberrant adenylate cyclase levels in hypertensive patients were restored toward normal following antihypertensive drug therapy (Marcil et al. (1996) *Hypertension* 28:83–90). In addition, studies of heart in human and animal models indicate adenylate cyclase has function in cardiomyopathy (Michael et al. (1995) *Hypertension* 25:962–970, Roth et al (1999) *Circulation* 99:3099–3099), ischemia (Sandhu et al. (1996) *Circulation Research* 78:137–147), myocardial infarction (Espinasse et al. (1999) *Cardiovascular Research* 42:87–98) and congestive heart failure (Kawahira et al. (1998) *Circulation* 98:262–267, Panza et al. (1995) *Circulation* 91:1732–1738). Additionally, studies have indicated that adenylate cyclase has function in clinical situations resulting in myocardial dysfunction such as cardiopulmonary bypass (Booth et al. (1998) *Anesthesiology* 89: 602–611). Decreased concentrations of adenylate cyclase also occur in chronic pacing-induced heart failure (Ishikawa et al. (1994) *J Clin Invest* 93:2224–9), whereas changes in activity of adenylate cyclase isoforms occur with activation of PKC (Kawabe et al. (1994) *J Biol Chem* 169: 16554–8), PKA (Chen et al.(1997) *PNAS* 94: 14100–4), aging and in pressure-overload failing right ventricles (Bristow et al. (1992) *J Clin Invest* 89:803–15).

As the enzyme that catalyzes conversion of intracellular ATP to cAMP, adenylate cyclase plays a central role in the regulation of cellular cAMP concentrations. Disruption or modulation of adenylate cyclase activity affects intracellular concentrations of cAMP, which can in turn modulate the cAMP signal transduction pathway. Modulation of this pathway can disrupt or alter cellular metabolism, growth, and differentiation, potentially leading to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma. Disorders associated with the tissues shown in FIG. 8 are also encompassed, especially skeletal muscle, heart, aorta, cervix, vein, brain, pancreas, and fetal kidney. Other disorders include tumors of the breast, lung, and colon. Disorders that are particularly relevant with respect to expression of the adenylate cyclase are cardiovascular disorders. As shown in FIG. 10, the adenylate cyclase is expressed in human cardiovascular tissues. Further, the gene is highly expressed in hypertrophic cardiac myocytes. Accordingly, disorders that are relevant include hypertension, atherosclerosis, ischemia, cardiomyopathy, congestive heart failure, myocardial infarction, and diseases of the cardiovascular system as disclosed herein.

The disclosed invention relates to methods and compositions for the modulation, diagnosis, and treatment of adenylate cyclase-associated or related disorders, particularly disorders resulting from aberrations in components of the cAMP signal transduction pathway, such as cAMP-dependent disorders, and disorders associated with cAMP-dependent protein kinases. Such disorders include, but are not limited to, disorders involving the skeletal muscle, heart, cervix, blood vessels, brain, pancreas, and cardiovascular system. Further relevant disorders include disorders involving the breast, and especially tumors of the breast.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effisions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_I$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex virus* Type 1, *Herpes simplex virus* Type 2, *Varicalla-zoster virus* (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erytematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders involving the ovary include, for example, polycystic ovarian disease, Stein-leventhal syndrome, Pseudomyxoma peritonei and stromal hypertchecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporois, paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, ewing saracoma, primitive neuroectodermal tumor, giant cell tumor, and metastatic tumors.

Specifically, the present invention provides isolated nucleic acid molecules comprising nucleotide sequences encoding the adenylate cyclase polypeptide whose amino acid sequence is given in SEQ ID NO:2, or a variant or fragment of the polypeptide. A nucleotide sequence encoding an adenylate cyclase polypeptide of the invention, more particularly the polypeptide of SEQ ID NO:2, is set forth in SEQ ID NO:1.

A novel human gene, termed clone h21529 is provided. This sequence, and complements thereof, are referred to as "adenylate cyclase" sequences indicating that the gene sequences share sequence similarity to adenylate cyclase genes.

The novel h21529 adenylate cyclase gene encodes an approximately 3.52 Kb mRNA transcript having the corresponding cDNA set forth in SEQ ID NO:1. This transcript has a 3231 nucleotide open reading frame (nucleotides 247–3477 of SEQ ID NO:1), which encodes a 1077 amino acid protein (SEQ ID NO:2). An analysis of the full-length h21529 polypeptide predicts that the N-terminal 50 amino acids may represent a region comprising a signal peptide. MEMSAT program analysis of the full-length h21529 polypeptide predicted transmembrane segments at amino acid residues (aa) 27–50, 61–79, 92–113, 120–136, 143–160, 174–190, 365–381, 408–424, 589–605, 612–631, 664–685, 713–736, 744–760, and 790–807. Transmembrane segments for the presumed mature peptide (aa 51–1077) were predicted at aa 11–29, 42–63, 70–86, 93–110, 124–140, 315–331, 358–374, 539–555, 562–581, 614–635, 663–686, 694–710, and 740–757. Prosite program analysis was used to predict various sites within the h21529 protein. N-glycosylation sites were predicted at aa 697–700, 704–707, 836–839, and 938–941, with the actual modified residue being the first amino acid. Protein kinase C phosphorylation sites were predicted at aa 6–8, 51–53, 202–204, 212–214, 218–220, 290–292, 526–528, 550–552, and 606–608, with the actual modified residue being the first amino acid. Casein kinase II phosphorylation sites were predicted at aa 51–54, 115–118, 202–205, 253–256, 290–293, 333–336, 359–362, 465–468, 495–498, 687–690, 878–881, 919–922, 941–944, 958–961, 968–971, and 1015–1018, with the actual modified residue being the first amino acid. Tyrosine kinase phosphorylation sites were predicted at aa 318–325, 437–444, 570–576, and 859–865, with the actual modified residue being the last amino acid. N-myristoylation sites were predicted at aa 35–40, 111–116, 137–142, 145–150, 184–189, 329–334, 345–350, 360–365, 368–373, 402–407, 412–417, 458–463, 654–659, 661–666, 936–941, 995–1000, 1008–1013, and 1055–1060, with the actual modified residue being the first amino acid. A prokaryotic membrane lipoprotein lipid attachment site was predicted at aa 745–755, and a leucine zipper pattern was predicted at aa 55–76. Guanylate cyclase signature sequences were predicted at aa 377–400 and 995–1018.

The h21529 adenylate cyclase protein possesses two adenylate/guanylate cyclase catalytic domains, from aa 264–448 and aa 864–1064, as predicted by HMMer, Version 2. Other domain matches predicted by HMMer included a copper/zinc superoxide dismutase domain, from aa 376–383, and a eubacterial secY protein domain, from aa 60–385.

The h21529 protein displays closest similarity to the rat adenylate cyclase IV (CYA4) (SP Accession Number P26770), approximately 86% identity over their 1075 amino acid overlap.

A plasmid containing the h21529 cDNA insert was deposited with the Patent Depository of the American Type Culture Collection (ATCC), 10801 University Boulevard, Manassas, Va., on Apr. 6, 2000, and assigned Patent Deposit Number PTA-1661. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The adenylate cyclase sequences of the invention are members of a family of molecules having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homolog of that protein of human origin, as well as a second, distinct protein of human origin and a murine homolog of that protein. Members of a family may also have common functional characteristics.

Preferred adenylate cyclase polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to adenylate cyclase nucleic acid molecules of the invention. BLAST protein searches can be performed with the XBLAST program, score=50, wordlength=3, to obtain amino acid sequences homologous to adenylate cyclase protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated adenylate cyclase proteins and polypeptides having an adenylate cyclase protein activity. As used interchangeably herein, a "adenylate cyclase protein activity", "biological activity of an adenylate cyclase protein", or "functional activity of an adenylate cyclase protein" refers to an activity exerted by an adenylate cyclase protein, polypeptide, or nucleic acid molecule on an adenylate cyclase responsive cell as determined in vivo, or in vitro, according to standard assay techniques. An adenylate cyclase activity can be a direct activity, such as conversion of intracellular ATP to cAMP, or an indirect activity, such as a cellular activity mediated by generation of cAMP, such as any downstream cellular response associated with the cAMP signal transduction pathway. In a preferred embodiment, an adenylate cyclase activity includes at least one or more of the following activities: (1) modulating (stimulating and/or enhancing or inhibiting) cellular growth, differentiation, and/or function, particularly in cells in which the sequences are expressed, as in FIGS. 7–10, for example, cells of the skeletal muscle, heart, cervix, vein, brain, pancreas, fetal kidney, and breast tumors, and cardiovascular tissue, such as that shown in FIG. 10; a protein kinase A cellular effect, such as release of hormones, glycogen metabolism, such as in liver, heart, and skeletal muscles; (2) modulating the cAMP signal transduction pathway; (3) modulating a target cell's cAMP concentration; (4) modulating cAMP-dependent protein kinase activity, such as protein kinase A; and (5) modulating the release of hormones, such as release of cortisol in the adrenal gland cells, thyroid hormones from the thyroid gland, testosterone from testicular Leydig cells, and melatonin from the pineal gland.

An "isolated" or "purified" adenylate cyclase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5N and 3N ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated adenylate cyclase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An adenylate cyclase protein that is substantially free of cellular material includes preparations of adenylate cyclase protein having less than about 30%, 20%, 10%, or 5% (by dry weight) of non-adenylate cyclase protein (also referred to herein as a "contaminating protein"). When the adenylate cyclase protein or biologically active portion thereof is recombinantly produced, preferably, culture medium represents less than about 30%, 20%, 10%, or 5% of the volume of the protein preparation. When adenylate cyclase protein is produced by chemical synthesis, preferably the protein preparations have less than about 30%, 20%, 10%, or 5% (by dry weight) of chemical precursors or non-adenylate cyclase chemicals.

Various aspects of the invention are described in further detail in the following subsections.

I. Isolated Nucleic Acid Molecules

One aspect of the invention pertains to isolated nucleic acid molecules comprising nucleotide sequences encoding adenylate cyclase proteins and polypeptides or biologically active portions thereof, as well as nucleic acid molecules sufficient for use as hybridization probes to identify adenylate cyclase-encoding nucleic acids (e.g., adenylate cyclase mRNA) and fragments for use as PCR primers for the amplification or mutation of adenylate cyclase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the adenylate cyclase proteins of the present invention include sequences set forth in SEQ ID NO:1, the nucleotide sequence of the cDNA insert of the plasmid deposited with the ATCC as Patent Deposit Number PTA-1661 (the "cDNA of Patent Deposit Number PTA-166 1"), and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the adenylate cyclase protein encoded by these nucleotide sequences is set forth in SEQ ID NO:2.

Nucleic acid molecules that are fragments of these adenylate cyclase nucleotide sequences are also encompassed by the present invention. By "fragment" is intended a portion of the nucleotide sequence encoding an adenylate cyclase protein. A fragment of an adenylate cyclase nucleotide sequence may encode a biologically active portion of an adenylate cyclase protein, or it may be a fragment that can be used as a hybridization probe or PCR primer using methods disclosed below. A biologically active portion of an adenylate cyclase protein can be prepared by isolating a portion of one of the adenylate cyclase nucleotide sequences of the invention, expressing the encoded portion of the adenylate cyclase protein (e.g., by recombinant expression in vitro), and assessing the activity of the encoded portion of the adenylate cyclase protein. Nucleic acid molecules that are fragments of an adenylate cyclase nucleotide sequence comprise at least 15, 20, 50, 75, 100, 200, 300, 350, 400, 450, 500, 550, 600, 650, 700, 750, 800, 850, 900, 950, 1000, 1050, 1100, 1200, 1300, 1400, 1500, 1600, 1700, 1800, 1900, 2000, 2250, 2500, 2750, 3,000, 3250, 3500, or up to the number of nucleotides present in a full-length adenylate cyclase nucleotide sequence disclosed herein (for example, 3518 nucleotides for SEQ ID NO:1) depending upon the intended use.

It is understood that isolated fragments of the nucleotide sequence, and the amino acid sequence encoded thereby, include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

For example, when considering the full-length, 3518 nucleotide transcript set forth in SEQ ID NO:1, the nucleotide sequence from about nucleotide (nt) 1 to about nt 200 encompasses isolated fragments greater than about 12, 15, or 20 nucleotides; the nucleotide sequence from about nt 200 to about nt 1781 encompasses isolated fragments greater than about 48, 50, or 55 nucleotides; the nucleotide sequence from about nt 1781 to about nt 2828 encompasses isolated fragments greater than about 28, 30, or 35 nucleotides; and the nucleotide sequence from about 2828 to about 3518 encompasses isolated fragments greater than about 453, 457, or 460 nucleotides.

A fragment of an adenylate cyclase nucleotide sequence that encodes a biologically active portion of an adenylate cyclase protein of the invention will encode at least 15, 25, 30, 50, 75, 100, 125, 150, 175, 200, 250, 300, 350, 400, 500, 600, 700, 800, 900, 1000, or 1050 contiguous amino acids, or up to the total number of amino acids present in a full-length adenylate cyclase protein of the invention (for example, 1077 amino acids for SEQ ID NO:2). Fragments of an adenylate cyclase nucleotide sequence that are useful as hybridization probes for PCR primers generally need not encode a biologically active portion of an adenylate cyclase protein.

Nucleic acid molecules that are variants of the adenylate cyclase nucleotide sequences disclosed herein are also encompassed by the present invention. "Variants" of the adenylate cyclase nucleotide sequences include those sequences that encode the adenylate cyclase proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the adenylate cyclase proteins disclosed in the present invention as discussed below. Generally, nucleotide sequence variants of the invention will have at least 45%, 55%, 65%, 75%, 85%, 95%, or 98% identity to a particular nucleotide sequence disclosed herein. A variant adenylate cyclase nucleotide sequence will encode an adenylate cyclase protein that has an amino acid sequence having at least 45%, 55%, 65%, 75%, 85%, 95%, or 98% identity to the amino acid sequence of an adenylate cyclase protein disclosed herein.

In addition to the adenylate cyclase nucleotide sequences shown in SEQ ID NOs:1 and 3, and the nucleotide sequence of the cDNA of Patent Deposit Number PTA-1661, it will be appreciated by those skilled in the art that DNA sequence polymorphisms that lead to changes in the amino acid sequences of adenylate cyclase proteins may exist within a population (e.g., the human population). Such genetic polymorphism in an adenylate cyclase gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an adenylate cyclase protein, preferably a mammalian adenylate cyclase protein. As used herein, the phrase "allelic variant" refers to a nucleotide sequence that occurs at an adenylate cyclase locus or to a polypeptide encoded by the nucleotide sequence. Such natural allelic variations can typically result in 1–5% variance in the nucleotide sequence of the adenylate cyclase gene. Any and all such nucleotide variations and resulting amino acid polymorphisms or variations in an adenylate cyclase sequence that are the result of natural allelic variation and that do not alter the functional activity of adenylate cyclase proteins are intended to be within the scope of the invention.

Moreover, nucleic acid molecules encoding adenylate cyclase proteins from other species (adenylate cyclase homologs), which have a nucleotide sequence differing from that of the adenylate cyclase sequences disclosed herein, are intended to be within the scope of the invention. For example, nucleic acid molecules corresponding to natural allelic variants and homologs of the human adenylate cyclase cDNA of the invention can be isolated based on their identity to the human adenylate cyclase nucleic acid disclosed herein using the human cDNA, or a portion thereof, as a hybridization probe according to standard hybridization techniques under stringent hybridization conditions as disclosed below.

In addition to naturally-occurring allelic variants of the adenylate cyclase sequences that may exist in the population, the skilled artisan will further appreciate that changes can be introduced by mutation into the nucleotide sequences of the invention thereby leading to changes in the amino acid sequence of the encoded adenylate cyclase proteins, without altering the biological activity of the adenylate cyclase proteins. Thus, an isolated nucleic acid molecule encoding an adenylate cyclase protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential"0 amino acid residue is a residue that can be altered from the wild-type sequence of an adenylate cyclase protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the adenylate/guanylate cyclase domain sequences of SEQ ID NO:2 (amino acid residues aa 264–448 and aa 864–1064), where such residues are essential for protein activity.

Alternatively, variant adenylate cyclase nucleotide sequences can be made by introducing mutations randomly along all or part of an adenylate cyclase coding sequence, such as by saturation mutagenesis, and the resultant mutants can be screened for adenylate cyclase biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The adenylate cyclase nucleotide sequences of the invention, and fragments and variants thereof, can be used as probes and/or primers to identify and/or clone adenylate cyclase homologs in other cell types, e.g., from other tissues, as well as adenylate cyclase homologs from other mammals. Such probes can be used to detect transcripts or genomic sequences encoding the same or identical proteins. These probes can be used as part of a diagnostic test kit for identifying cells or tissues that misexpress an adenylate cyclase protein, such as by measuring levels of an adenylate cyclase-encoding nucleic acid in a sample of cells from a subject, e.g., detecting adenylate cyclase mRNA levels or determining whether a genomic adenylate cyclase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols. A Guide to Methods and Applications* (Academic Press, NY). Adenylate cyclase nucleotide sequences isolated based on their sequence identity to the adenylate cyclase nucleotide sequences set forth herein or to fragments and variants thereof are encompassed by the present invention.

In a hybridization method, all or part of a known adenylate cyclase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known adenylate cyclase nucleotide sequence disclosed herein. Degenerate primers designed on the basis of conserved nucleotides or amino acid residues in a known adenylate cyclase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an adenylate cyclase nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified adenylate cyclase nucleic acid molecule hybridizes under stringent conditions to a probe that is a nucleic acid molecule comprising one of the adenylate cyclase nucleotide sequences of the invention or a fragment thereof. In another embodiment, the previously unknown adenylate cyclase nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the adenylate cyclase nucleotide sequences disclosed herein or a fragment thereof.

Accordingly, in another embodiment, an isolated previously unknown adenylate cyclase nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, the cDNA of Patent Deposit Number PTA-1661, or a complement, fragment, or variant thereof.

As used herein, the term "hybridizes under stringent conditions" is intended to describe conditions for hybridization and washing under which nucleotide sequences having at least 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization conditions is hybridization in 6×sodium chloride/sodium citrate (SSC) at about 45° C., followed by one or more washes in 0.2×SSC, 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to an adenylate cyclase sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the adenylate cyclase nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the adenylate cyclase nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire adenylate cyclase coding strand, or to only a portion thereof, e.g., all or part of the protein coding region (or open reading frame). An antisense nucleic acid molecule can be antisense to a noncoding region of the coding strand of a nucleotide sequence encoding an adenylate cyclase protein. The noncoding regions are the 5' and 3' sequences that flank the coding region and are not translated into amino acids.

Given the coding-strand sequence encoding an adenylate cyclase protein disclosed herein (e.g., SEQ ID NO:1), antisense nucleic acids of the invention can be designed according to the rules of Watson and Crick base pairing. The antisense nucleic acid molecule can be complementary to the entire coding region of adenylate cyclase mRNA, but more preferably is an oligonucleotide that is antisense to only a portion of the coding or noncoding region of adenylate cyclase mRNA. For example, the antisense oligonucleotide can be complementary to the region surrounding the translation start site of adenylate cyclase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an adenylate cyclase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave adenylate cyclase mRNA transcripts to thereby inhibit translation of adenylate cyclase mRNA. A ribozyme having specificity for an adenylate cyclase-encoding nucleic acid can be designed based upon the nucleotide sequence of an adenylate cyclase cDNA disclosed herein (e.g., SEQ ID NO:1). See, e.g., Cech et al., U.S. Pat. No. 4,987,071; and Cech et al., U.S. Pat. No. 5,116,742. Alternatively, adenylate cyclase mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, adenylate cyclase gene expression can be inhibited by targeting nucleotide sequences complementary to the regulatory region of the adenylate cyclase protein (e.g., the adenylate cyclase promoter and/or enhancers) to form triple helical structures that prevent transcription of the adenylate cyclase gene in target cells. See generally Helene (1991) *Anticancer Drug Des.* 6(6):569; Helene (1992) *Ann. N.Y. Acad. Sci.* 660:27; and Maher (1992) Bioassays 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of an adenylate cyclase molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of an adenylate cyclase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated Adenylate Cyclase Proteins and Anti-adenylate Cyclase Antibodies

Adenylate cyclase proteins are also encompassed within the present invention. By "adenylate cyclase protein" is intended a protein having the amino acid sequence set forth in SEQ ID NO: 2, as well as fragments, biologically active portions, and variants thereof. "Fragments" or "biologically active portions" include polypeptide fragments suitable for use as immunogens to raise anti-adenylate cyclase antibodies. Fragments include peptides comprising amino acid sequences sufficiently identical to or derived from the amino acid sequence of an adenylate cyclase protein of the invention and exhibiting at least one activity of an adenylate cyclase protein, but which include fewer amino acids than the full-length (SEQ ID NO:2) adenylate cyclase protein disclosed herein. Typically, biologically active portions comprise a domain or motif with at least one activity of the adenylate cyclase protein. A biologically active portion of an adenylate cyclase protein can be a polypeptide that is, for example, 10, 25, 50, 100 or more amino acids in length. Such biologically active portions can be prepared by recombinant techniques and evaluated for one or more of the functional activities of a native adenylate cyclase protein. As used here, a fragment not previously disclosed comprises at least about 100, 102, or 105 contiguous amino acids of SEQ ID NO:2. The invention encompasses other fragments, however, such as any fragment in the protein greater than 6, 7, 8, or 9 amino acids, where not previously disclosed, depending upon the intended use.

By "variants" is intended proteins or polypeptides having an amino acid sequence that is at least about 45%, 55%, 65%, preferably about 75%, 85%, 95%, or 98% identical to the amino acid sequence of SEQ ID NO:2. Variants also include polypeptides encoded by the cDNA insert of the plasmid deposited with ATCC as Patent Deposit Number PTA-1661, or polypeptides encoded by a nucleic acid molecule that hybridizes to the nucleic acid molecule of SEQ ID NO:1, or a complement thereof, under stringent conditions. Such variants generally retain the functional activity of the adenylate cyclase proteins of the invention. Variants include polypeptides that differ in amino acid sequence due to natural allelic variation or mutagenesis.

The invention also provides adenylate cyclase chimeric or fusion proteins. As used herein, an adenylate cyclase "chimeric protein" or "fusion protein" comprises an adenylate cyclase polypeptide operably linked to a non-adenylate cyclase polypeptide. A "adenylate cyclase polypeptide" refers to a polypeptide having an amino acid sequence corresponding to an adenylate cyclase protein, whereas a "non-adenylate cyclase polypeptide" refers to a polypeptide having an amino acid sequence corresponding to a protein that is not substantially identical to the adenylate cyclase protein, e.g., a protein that is different from the adenylate cyclase protein and which is derived from the same or a different organism. Within an adenylate cyclase fusion protein, the adenylate cyclase polypeptide can correspond to all or a portion of an adenylate cyclase protein, preferably at least one biologically active portion of an adenylate cyclase protein. Within the fusion protein, the term "operably linked" is intended to indicate that the adenylate cyclase polypeptide and the non-adenylate cyclase polypeptide are fused in-frame to each other. The non-adenylate cyclase polypeptide can be fused to the N-terminus or C-terminus of the adenylate cyclase polypeptide.

One useful fusion protein is a GST-adenylate cyclase fusion protein in which the adenylate cyclase sequences are fused to the C-terminus of the GST sequences. Such fusion proteins can facilitate the purification of recombinant adenylate cyclase proteins.

In yet another embodiment, the fusion protein is an adenylate cyclase-immunoglobulin fusion protein in which all or part of an adenylate cyclase protein is fused to sequences derived from a member of the immunoglobulin protein family. The adenylate cyclase-immunoglobulin fusion proteins of the invention can be incorporated into pharmaceutical compositions and administered to a subject to inhibit an interaction between an adenylate cyclase ligand and an adenylate cyclase protein on the surface of a cell, thereby suppressing adenylate cyclase-mediated signal transduction in vivo. The adenylate cyclase-immunoglobulin fusion proteins can be used to affect the bioavailability of an adenylate cyclase cognate ligand. Inhibition of the adenylate cyclase ligand/adenylate cyclase interaction may be useful therapeutically, both for treating proliferative and differentiative disorders and for modulating (e.g., promoting or inhibiting) cell survival. Moreover, the adenylate cyclase-immunoglobulin fusion proteins of the invention can be used as immunogens to produce anti-adenylate cyclase antibodies in a subject, to purify adenylate cyclase ligands, and in screening assays to identify molecules that inhibit the interaction of an adenylate cyclase protein with an adenylate cyclase ligand.

Preferably, an adenylate cyclase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, an adenylate cyclase-encoding nucleic acid can be cloned into a commercially available expression vector such that it is linked in-frame to an existing fusion moiety.

Variants of the adenylate cyclase proteins can function as either adenylate cyclase agonists (mimetics) or as adenylate cyclase antagonists. Variants of the adenylate cyclase protein can be generated by mutagenesis, e.g., discrete point mutation or truncation of the adenylate cyclase protein. An agonist of the adenylate cyclase protein can retain substantially the same, or a subset, of the biological activities of the naturally occurring form of the adenylate cyclase protein. An antagonist of the adenylate cyclase protein can inhibit one or more of the activities of the naturally occurring form of the adenylate cyclase protein by, for example, competitively binding to a downstream or upstream member of a cellular signaling cascade that includes the adenylate cyclase protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the adenylate cyclase proteins.

Variants of an adenylate cyclase protein that function as either adenylate cyclase agonists or as adenylate cyclase antagonists can be identified by screening combinatorial libraries of mutants, e.g., truncation mutants, of an adenylate cyclase protein for adenylate cyclase protein agonist or antagonist activity. In one embodiment, a variegated library of adenylate cyclase variants is generated by combinatorial mutagenesis at the nucleic acid level and is encoded by a variegated gene library. A variegated library of adenylate cyclase variants can be produced by, for example, enzymatically ligating a mixture of synthetic oligonucleotides into gene sequences such that a degenerate set of potential adenylate cyclase sequences is expressible as individual polypeptides, or alternatively, as a set of larger fusion proteins (e.g., for phage display) containing the set of adenylate cyclase sequences therein. There are a variety of methods that can be used to produce libraries of potential adenylate cyclase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential adenylate cyclase sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of an adenylate cyclase protein coding sequence can be used to generate a variegated population of adenylate cyclase fragments for screening and subsequent selection of variants of an adenylate cyclase protein. In one embodiment, a library of coding sequence fragments can be generated by treating a double-stranded PCR fragment of an adenylate cyclase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the adenylate cyclase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of adenylate cyclase proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify adenylate cyclase variants (Arkin and Yourvan (1992) *Proc. Natl. Acad. Sci. USA* 89:7811–7815; Delgrave et al. (1993) *Protein Engineering* 6(3):327–331).

An isolated adenylate cyclase polypeptide of the invention can be used as an immunogen to generate antibodies that bind adenylate cyclase proteins using standard techniques for polyclonal and monoclonal antibody preparation. The full-length adenylate cyclase protein can be used or, alternatively, the invention provides antigenic peptide fragments of adenylate cyclase proteins for use as immunogens. The antigenic peptide of an adenylate cyclase protein comprises at least 8, preferably 10, 15, 20, or 30 amino acid residues of the amino acid sequence shown in SEQ ID NO:2 and encompasses an epitope of an adenylate cyclase protein such that an antibody raised against the peptide forms a specific immune complex with the adenylate cyclase protein. Preferred epitopes encompassed by the antigenic peptide are regions of a adenylate cyclase protein that are located on the surface of the protein, e.g., hydrophilic regions.

Accordingly, another aspect of the invention pertains to anti-adenylate cyclase polyclonal and monoclonal antibodies that bind an adenylate cyclase protein. Polyclonal anti-adenylate cyclase antibodies can be prepared by immunizing a suitable subject (e.g., rabbit, goat, mouse, or other mammal) with an adenylate cyclase immunogen. The anti-adenylate cyclase antibody titer in the immunized subject can be monitored over time by standard techniques, such as with an enzyme linked immunosorbent assay (ELISA) using immobilized adenylate cyclase protein. At an appropriate time after immunization, e.g., when the anti-adenylate cyclase antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-adenylate cyclase antibody can be identified and isolated by screening a recombinant combinatorial immunoglobulin library (e.g., an antibody phage display library) with an adenylate cyclase protein to thereby isolate immunoglobulin library members that bind the adenylate cyclase protein. Kits for generating and screening phage display libraries are commercially available (e.g., the Pharmacia *Recombinant Phage Antibody System*, Catalog No. 27-9400-01; and the Stratagene SurfZAP® *Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-adenylate cyclase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-adenylate cyclase antibody (e.g., monoclonal antibody) can be used to isolate adenylate cyclase proteins by standard techniques, such as affinity chromatography or immunoprecipitation. An anti-adenylate cyclase antibody can facilitate the purification of natural adenylate cyclase protein from cells and of recombinantly produced adenylate cyclase protein expressed in host cells. Moreover, an anti-adenylate cyclase antibody can be used to detect adenylate cyclase protein (e.g., in a cellular lysate or cell supernatant) in order to evaluate the abundance and pattern of expression of the adenylate cyclase protein. Anti-adenylate cyclase antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriaziny-lamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al.(1985) "Monoclonal Antibodies for Immunotargeting of Drugs in Cancer Therapy," in *Monoclonal Antibodies And Cancer Therapy*, ed. Reisfeld et al. (Alan R. Liss, Tnc.), pp. 243–56); Hellstrom et al. (1987) "Antibodies for Drug Delivery," in *Controlled Drug Delivery*, ed. Robinson et al. (2d ed., Marcel Dekker, Inc.), pp. 623–53; Thorpe (1985) "Antibody Carriers of Cytotoxic Agents in Cancer Therapy: A Review", in *Monoclonal Antibodies '84:Biological And Clinical Applications*, ed. Pinchera et al., pp. 475–506; "Analysis, Results, and Future Prospective of the Therapeutic Use of Radiolabeled Antibody in Cancer Therapy," in *Monoclonal Antibodies For Cancer Detection And Therapy*, ed. Baldwin et al. (Academic Press, NY), pp. 303–316; and Thorpe et al. (1982) *Immunol. Rev.* 62:119–58. Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding an adenylate cyclase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., adenylate cyclase proteins, mutant forms of adenylate cyclase proteins, fusion proteins, etc.).

The recombinant expression vectors of the invention can be designed for expression of adenylate cyclase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kuran and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Grass (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to adenylate cyclase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics,* Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an adenylate cyclase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) adenylate cyclase protein. Accordingly, the invention further provides methods for producing adenylate cyclase protein using the host cells of the invention. In one embodiment, the method comprises culturing the host cell of the invention, into which a recombinant expression vector encoding an adenylate cyclase protein has been introduced, in a suitable medium such that adenylate cyclase protein is produced. In another embodiment, the method further comprises isolating adenylate cyclase protein from the medium or the host cell.

The host cells of the invention can also be used to produce nonhuman transgenic animals. For example, in one embodiment, a host cell of the invention is a fertilized oocyte or an embryonic stem cell into which adenylate cyclase-coding sequences have been introduced. Such host cells can then be used to create nonhuman transgenic animals in which exogenous adenylate cyclase sequences have been introduced into their genome or homologous recombinant animals in which endogenous adenylate cyclase sequences have been altered. Such animals are useful for studying the function and/or activity of adenylate cyclase genes and proteins and for identifying and/or evaluating modulators of adenylate cyclase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous adenylate cyclase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing adenylate cyclase-encoding nucleic acid into the male pronuclei of a fertilized oocyte, e.g., by microinjection, retroviral infection, and allowing the oocyte to develop in a pseudopregnant female foster animal. The adenylate cyclase cDNA sequence can be introduced as a transgene into the genome of a nonhuman animal. Alternatively, a homolog of the mouse adenylate cyclase gene can be isolated based on hybridization and used as a transgene. Intronic sequences and polyadenylation signals can also be included in the transgene to increase the efficiency of expression of the transgene. A tissue-specific regulatory sequence(s) can be operably linked to the adenylate cyclase transgene to direct expression of adenylate cyclase protein to particular cells. Methods for generating transgenic animals via embryo manipulation and microinjection, particularly animals such as mice, have become conventional in the art and are described, for example, in U.S. Pat. Nos. 4,736,866, 4,870, 009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the adenylate cyclase transgene in its genome and/or expression of adenylate cyclase mRNA in tissues or cells of the animals. A transgenic founder animal can then be used to breed additional animals carrying the transgene. Moreover, transgenic animals carrying a transgene encoding adenylate cyclase gene can further be bred to other transgenic animals carrying other transgenes.

Homologously recombinant host cells can also be produced that allow the in situ alteration of endogenous polynucleotide sequences of the invention in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the polynucleotides or sequences of the invention proximal or distal to a gene of the invention are allowed to integrate into a host cell genome by homologous recombination where expression of the gene can be affected. In one embodiment, regulatory sequences are introduced that either increase or decrease expression of an endogenous sequence. Accordingly, a protein of the invention can be produced in a cell not normally producing it. Alternatively, increased expression of a protein of the invention can be effected in a cell normally producing the protein at a specific level. Further, expression can be decreased or eliminated by introducing a specific regulatory sequence. The regulatory sequence can be heterologous to the protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant proteins of the invention. Such mutations could be introduced, for example, into the specific functional regions such as the ligand-binding site.

To create a homologous recombinant animal, one prepares a vector containing at least a portion of an adenylate cyclase gene or a homolog of the gene into which a deletion, addition, or substitution has been introduced to thereby alter, e.g., functionally disrupt, the adenylate cyclase gene. In a preferred embodiment, the vector is designed such that, upon homologous recombination, the endogenous adenylate cyclase gene is functionally disrupted (i.e., no longer encodes a functional protein; also referred to as a "knock out" vector). Alternatively, the vector can be designed such that, upon homologous recombination, the endogenous adenylate cyclase gene is mutated or otherwise altered but still encodes functional protein (e.g., the upstream regulatory region can be altered to thereby alter the expression of the endogenous adenylate cyclase protein). In the homologous recombination vector, the altered portion of the adenylate cyclase gene is flanked at its 5' and 3' ends by additional nucleic acid of the adenylate cyclase gene to allow for homologous recombination to occur between the exogenous adenylate cyclase gene carried by the vector and an endogenous adenylate cyclase gene in an embryonic stem cell. The additional flanking adenylate cyclase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced adenylate cyclase gene has homologously recombined with the endogenous adenylate cyclase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach,* ed. Robertson (IRL, Oxford), pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

IV. Pharmaceutical Compositions

The adenylate cyclase nucleic acid molecules, adenylate cyclase proteins, and anti-adenylate cyclase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the adenylate cyclase-associated or related disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents that modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an adenylate cyclase protein or anti-adenylate cyclase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

Figure 2:
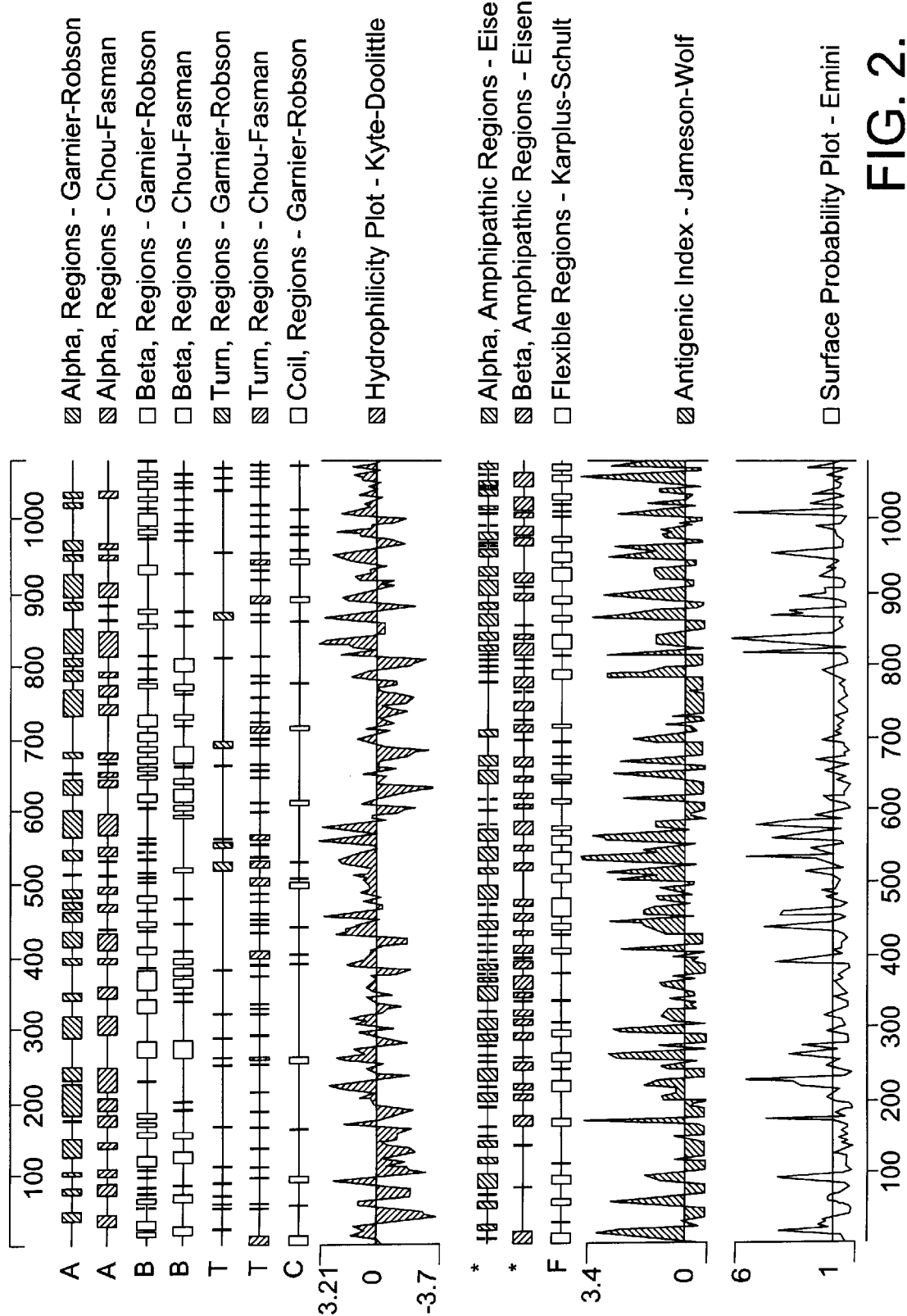
FIG. 2 shows an analysis of the 21529 amino acid sequence: αβ turn and coil regions; hydrophilicity; amphipathic regions; flexible regions; antigenic index; and surface probability plot.
Figure 3:
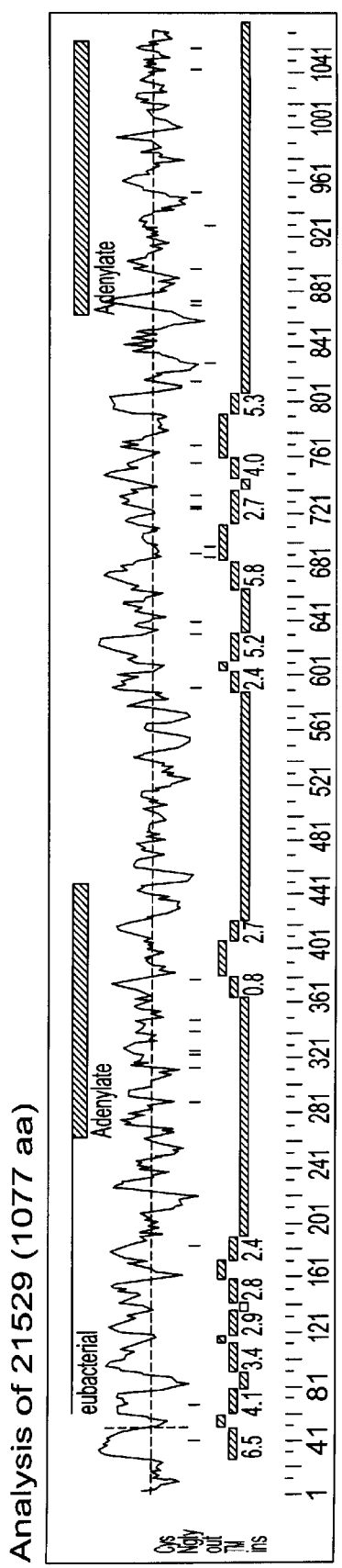
FIG. 3 shows the 21529 protein hydrophobicity plot.
Figure 5:
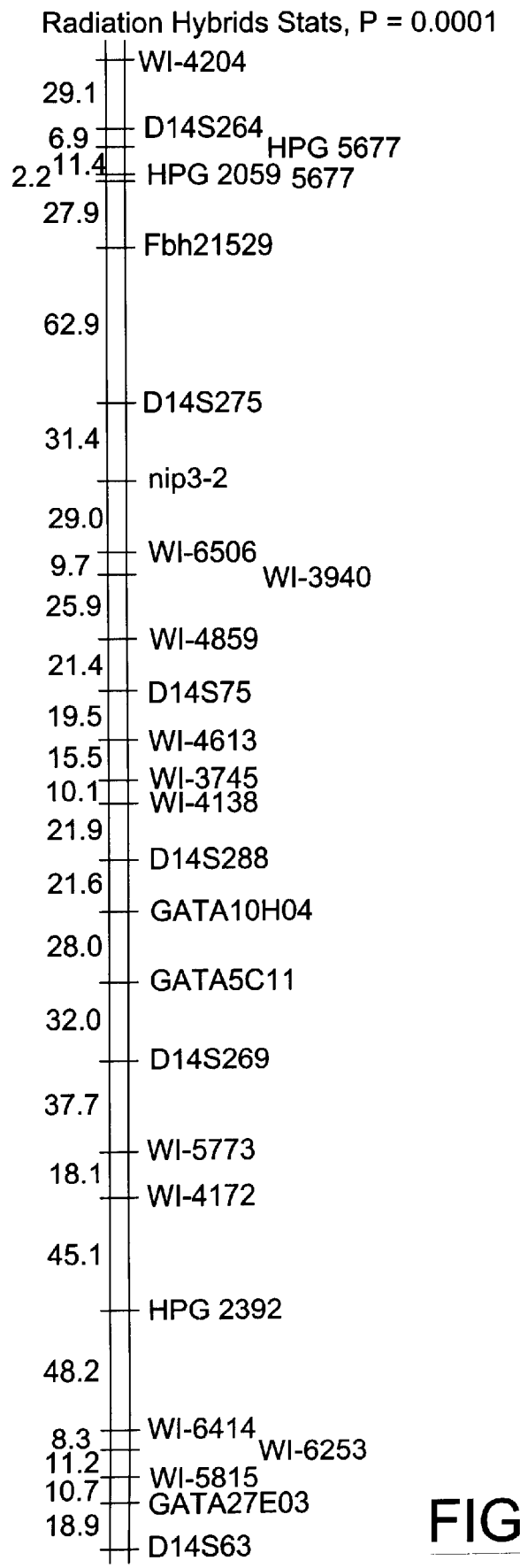
FIG. 5 shows the approximate chromosomal location of the 21529 gene as well as markers in that region.
Figure 7:
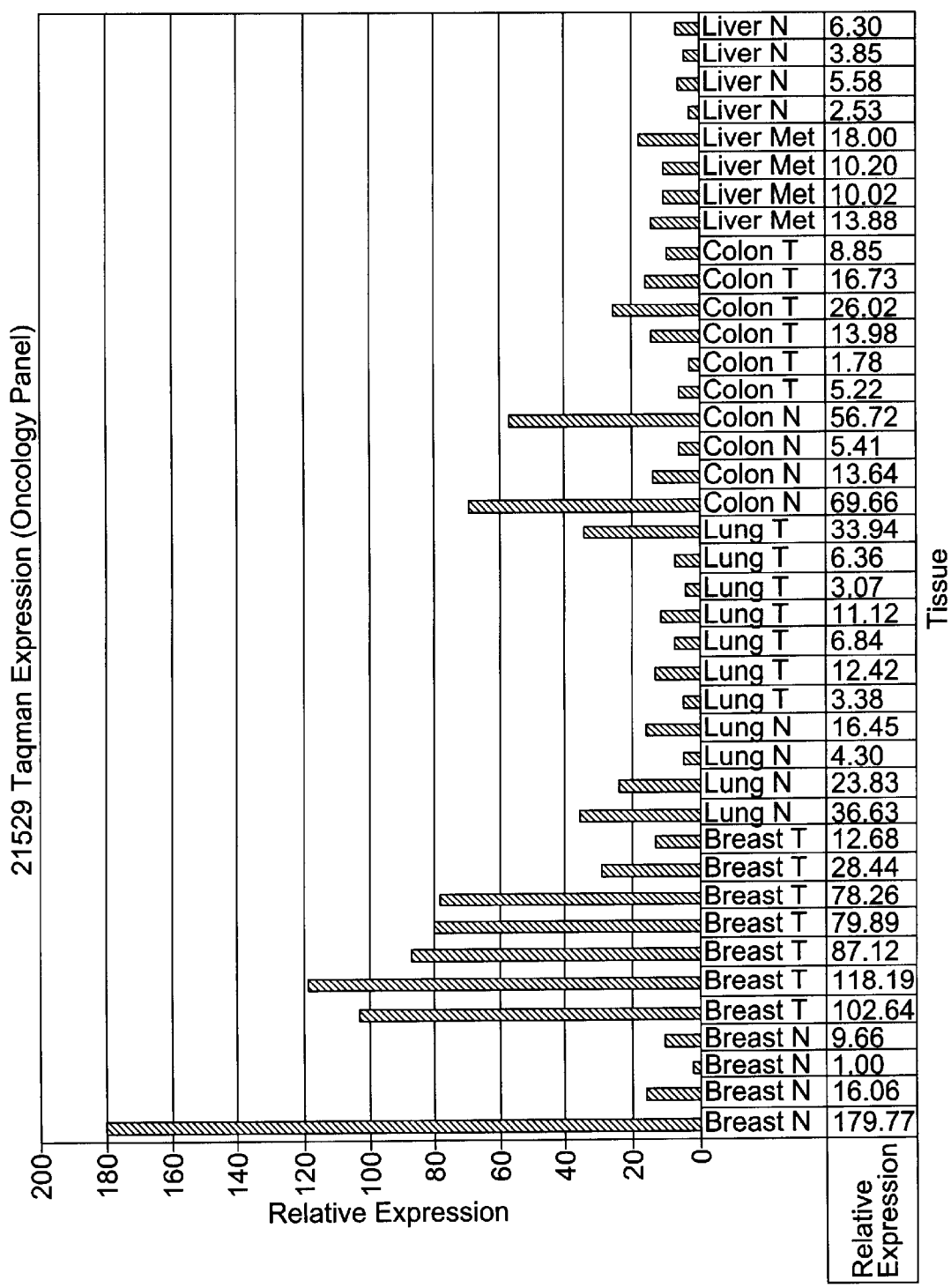
FIG. 7 indicates expression of the 21529 gene in normal and corresponding tumor tissues.

The diagnostic, therapeutic and other uses and methods of the invention pertain to cells and tissues in which expression of the adenylate cyclase is relevant. First, relevant tissues and cells include those in which the protein is expressed. FIG. 7 shows expression of the protein in various normal human tissues. Thus, the methods are relevant to those tissues. Expression is especially high in several of these tissues, for example, skeletal muscle, heart, cervix, vein, brain, and pancreas. Accordingly, the methods are especially relevant to these issues. Significant expression is also found in liver, thyroid, ovary, aorta, placenta, breast, fetal kidney, and fetal heart. Moreover, the methods are relevant to tissues in which there is even lower expression of the gene and to disorders of these tissues. Such disorders include, but are not limited to, those discussed herein above. The methods are of particular relevance in breast carcinoma, which shows highly increased levels of the gene. See FIGS. 7 and 9. Moreover, expression is relevant to lung carcinoma, in which a decreased expression of the gene is found. See FIGS. 7 and 9. Further, significantly decreased expression is seen in colon tumor compared to normal colon tissue, indicating the relevance of the methods to colon carcinoma. Finally, the gene is relatively highly expressed in colonic liver metastases. Accordingly, the methods are also specifically relevant to this condition. Furthermore, expression of the gene is shown in several human cardiovascular tissues. See FIG. 10. These include, but are not limited to, heart, aorta, coronary artery, aorta with intimal proliferation (atheroplaques), internal mammary artery, heart tissue from congestive heart failure patients, heart tissue from ischemic patients, heart tissue from myopathic patients, and saphenous vein. Accordingly, the methods disclosed herein are particularly relevant to treatment, diagnosis, and other uses involving expression of the gene in these tissues.

The nucleic acid molecules, proteins, protein homologs, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express adenylate cyclase protein (e.g., via a recombinant expression vector in a host cell in gene therapy applications), to detect adenylate cyclase mRNA (e.g., in a biological sample) or a genetic lesion in an adenylate cyclase gene, and to modulate adenylate cyclase activity. In addition, the adenylate cyclase proteins can be used to screen drugs or compounds that modulate the immune response as well as to treat disorders characterized by insufficient or excessive production of adenylate cyclase protein or production of adenylate cyclase protein forms that have decreased or aberrant activity compared to adenylate cyclase wild type protein. In addition, the anti-adenylate cyclase antibodies of the invention can be used to detect and isolate adenylate cyclase proteins and modulate adenylate cyclase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to adenylate cyclase proteins or have a stimulatory or inhibitory effect on, for example, adenylate cyclase expression or adenylate cyclase activity.

Effectors of adenylate cyclase modulate activity via a decrease in catalytic function, a decrease in total protein concentration or through an alteration in an adenylate cyclase isoform. Effectors of adenylate cyclase include upstream components of the cAMP signal transduction pathway including, but not limited to, catecholamines such as epinephrine and norepinephrine, Beta adrenergic receptors (βAR), and G proteins including inhibitory and stimulatory subunits and their various isoforms. Additional modulators include components of the RAS system, the sympathetic nervous system, m-cholinoceptors (m-Ch), protein kinase A (Iwami et al. (1995) *J Biol Chem* 270:12481–12484) and adenosine receptors.

Additional modulators of adenylate cyclase include, for example, pertusis toxin, captopril, nitrendipine, captopril plus nitrendipine, forskolin, isoproterenol, guanylylimidodiphosphate (Gpp(NH)p), prostacylin mimetic cicaprost, NECA, PGE sub 1, NK-H477, zinterol, NaF, magnesium, $H_2O_2$, C-ANF sub 4–23, βAR receptors antagonists, propranol, and fentanyl and other opiods.

The cAMP produced by adenylate cyclase cAMP subsequently influences multiple cellular components which influence cardiovascular physiology including, for example, protein kinase A, voltage dependant C-type Ca channels, adenosine and inosine, adenosine receptors and phospholamban. Furthermore, cAMP influences transcription factors such as CREB and CREM (Delmas et al. (1994) *Rev Physiol Biochem Pharmacol* 124: 1–28), influences expression of cytokine induced adhesion molecules on smooth muscle cells (Braun et al. (1997) *Arteriosclerosis, Thrombosis and Vascular Biology* 17:2568–2575), influences phosphorylation of cardiac tryponin 1 by cAMP dependant protein kinase A, and influences DNA synthesis and vascular smooth muscle cell growth in neonatal smooth muscle cells (Dubey et al. (1996) *Hypertension* 28:765–771).

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the adenylate cyclase protein can be accomplished, for example, by coupling the test compound with a radioisotope or enzymatic label such that binding of the test compound to the adenylate cyclase protein or biologically active portion thereof can be determined by detecting the labeled compound in a complex. For example, test compounds can be labeled with $^{125}I$, $^{35}S$, $^{14}C$, or $^3H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the adenylate cyclase protein to bind to or interact with an adenylate cyclase target molecule. By "target molecule" is intended a molecule with which an adenylate cyclase protein binds or interacts in nature. In a preferred embodiment, the ability of the adenylate cyclase protein to bind to or interact with an adenylate cyclase target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., an adenylate cyclase-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting an adenylate cyclase protein or biologically active portion thereof with a test compound and determining the ability of the test compound to bind to the adenylate cyclase protein or biologically active portion thereof. Binding of the test compound to the adenylate cyclase protein can be determined either directly or indirectly as described above. In a preferred embodiment, the assay includes contacting the adenylate cyclase protein or biologically active portion thereof with a known compound that binds adenylate cyclase protein to form an assay mixture, contacting the assay mixture with a test compound, and determining the ability of the test compound to preferentially bind to adenylate cyclase protein or biologically active portion thereof as compared to the known compound.

In another embodiment, an assay is a cell-free assay comprising contacting adenylate cyclase protein or biologically active portion thereof with a test compound and determining the ability of the test compound to modulate (e.g., stimulate or inhibit) the activity of the adenylate cyclase protein or biologically active portion thereof. Determining the ability of the test compound to modulate the activity of an adenylate cyclase protein can be accomplished, for example, by determining the ability of the adenylate cyclase protein to bind to an adenylate cyclase target molecule as described above for determining direct binding. In an alternative embodiment, determining the ability of the test compound to modulate the activity of an adenylate cyclase protein can be accomplished by determining the ability of the adenylate cyclase protein to further modulate an adenylate cyclase target molecule. For example, the catalytic/enzymatic activity of the target molecule on an appropriate substrate can be determined as previously described.

In yet another embodiment, the cell-free assay comprises contacting the adenylate cyclase protein or biologically active portion thereof with a known compound that binds an adenylate cyclase protein to form an assay mixture, contacting the assay mixture with a test compound, and determining the ability of the test compound to preferentially bind to or modulate the activity of an adenylate cyclase target molecule.

Whole cell assays include, but are not limited to, for cardiovascular function, transfection into mammalian vascular smooth muscle cells. These include, for example, A10 cells. In one embodiment, human cells are transfected. Generally, however, for screening adenylate cyclase, other mammalian cells, such as COS and CHO, are available. These cells can be assayed, for example, for a cAMP-mediated response. This would include, but is not limited to, measuring cAMP inducible genes, such as FOS. Assays for these responses include those, but are not limited to those, otherwise described herein, in any of the references cited herein relevant to cAMP assays. These references are incorporated herein in pertinent part for cAMP assays. As another example, an element responsive to cAMP levels can be placed in operational structure to a luciferase read out system and the cAMP level can then be measured by means of fluorescence.

In addition to whole cell assays, biochemical enzymatic assays are also available, such as those disclosed herein, in the references cited herein, which are incorporated by reference with respect to the teachings pertaining to biochemical enzymatic assays. Thus, such assays include, but are not limited to, the generation of recombinant adenylate cyclase in bacteria, baculovirus, or mammalian cells, as discussed in detail herein. Since there are two catalytic sites in adenylate cyclase, either one or both of the sites may be expressed. Such biochemical enzymatic assays also include measurement of the cAMP:ATP ratio, which can be measured by well known methods using luciferase.

In the above-mentioned assays, it may be desirable to immobilize either an adenylate cyclase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/adenylate cyclase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or adenylate cyclase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of adenylate cyclase binding or activity determined using standard techniques.

Other techniques for immobilizing proteins on matrices can also be used in the screening assays of the invention. For example, either adenylate cyclase protein or its target molecule can be immobilized utilizing conjugation of biotin and streptavidin. Biotinylated adenylate cyclase molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with an adenylate cyclase protein or target molecules but which do not interfere with binding of the adenylate cyclase protein to its target molecule can be derivatized to the wells of the plate, and unbound target or adenylate cyclase protein trapped in the wells by antibody conjugation. Methods for detecting such complexes, in addition to those described above for the GST-immobilized complexes, include immunodetection of complexes using antibodies reactive with the adenylate cyclase protein or target molecule, as well as enzyme-linked assays that rely on detecting an enzymatic activity associated with the adenylate cyclase protein or target molecule.

In another embodiment, modulators of adenylate cyclase expression are identified in a method in which a cell is contacted with a candidate compound and the expression of adenylate cyclase mRNA or protein in the cell is determined relative to expression of adenylate cyclase mRNA or protein in a cell in the absence of the candidate compound. When expression is greater (statistically significantly greater) in the presence of the candidate compound than in its absence, the candidate compound is identified as a stimulator of adenylate cyclase mRNA or protein expression. Alternatively, when expression is less (statistically significantly less) in the presence of the candidate compound than in its absence, the candidate compound is identified as an inhibitor of adenylate cyclase mRNA or protein expression. The level of adenylate cyclase mRNA or protein expression in the cells can be determined by methods described herein for detecting adenylate cyclase mRNA or protein.

In yet another aspect of the invention, the adenylate cyclase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with adenylate cyclase protein ("adenylate cyclase-binding proteins" or "adenylate cyclase-bp") and modulate adenylate cyclase activity. Such adenylate cyclase-binding proteins are also likely to be involved in the propagation of signals by the adenylate cyclase proteins as, for example, upstream or downstream elements of the adenylate cyclase pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial adenylate cyclase gene sequences of the invention can be used to map their respective adenylate cyclase genes on a chromosome, thereby facilitating the location of gene regions associated with a genetic disease. Computer analysis of adenylate cyclase sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the adenylate cyclase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map an adenylate cyclase sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, N.Y.). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the adenylate cyclase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The adenylate cyclase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the adenylate cyclase sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The adenylate cyclase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:1, is used, a more appropriate number of primers for positive individual identification would be 500 to 2,000.

3. Use of Partial Adenylate Cyclase Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the adenylate cyclase sequences or portions thereof, e.g., fragments derived from the noncoding regions of SEQ ID NO:1 having a length of at least 20 or 30 bases.

The adenylate cyclase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such adenylate cyclase probes, can be used to identify tissue by species and/or by organ type.

In a similar fashion, these reagents, e.g., adenylate cyclase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting adenylate cyclase protein and/or nucleic acid expression as well as adenylate cyclase activity, in the context of a biological sample. An exemplary method for detecting the presence or absence of adenylate cyclase proteins in a biological sample involves obtaining a biological sample from a test subject and contacting the biological sample with a compound or an agent capable of detecting adenylate cyclase protein or nucleic acid (e.g., mRNA, genomic DNA) that encodes adenylate cyclase protein such that the presence of adenylate cyclase protein is detected in the biological sample. Results obtained with a biological sample from the test subject may be compared to results obtained with a biological sample from a control subject.

A preferred agent for detecting adenylate cyclase mRNA or genomic DNA is a labeled nucleic acid probe capable of hybridizing to adenylate cyclase mRNA or genomic DNA. The nucleic acid probe can be, for example, a full-length adenylate cyclase nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to adenylate cyclase mRNA or genomic DNA. Other suitable probes for use in the diagnostic assays of the invention are described herein.

A preferred agent for detecting adenylate cyclase protein is an antibody capable of binding to adenylate cyclase protein, preferably an antibody with a detectable label. Antibodies can be polyclonal, or more preferably, monoclonal. An intact antibody, or a fragment thereof (e.g., Fab or F(abN)$_2$ )can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect adenylate cyclase mRNA, protein, or genomic DNA in a biological sample in vitro as well as in vivo. For example, in vitro techniques for detection of adenylate cyclase mRNA include Northern hybridizations and in situ hybridizations. In vitro techniques for detection of adenylate cyclase protein include enzyme linked immunosorbent assays (ELISAs), Western blots, immunoprecipitations, and immunofluorescence. In vitro techniques for detection of adenylate cyclase genomic DNA include Southern hybridizations. Furthermore, in vivo techniques for detection of adenylate cyclase protein include introducing into a subject a labeled anti-adenylate cyclase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

The invention also encompasses kits for detecting the presence of adenylate cyclase proteins in a biological sample (a test sample). Such kits can be used to determine if a subject is suffering from or is at increased risk of developing a disorder associated with aberrant expression of adenylate cyclase protein (e.g., an immunological disorder). For example, the kit can comprise a labeled compound or agent capable of detecting adenylate cyclase protein or mRNA in a biological sample and means for determining the amount of an adenylate cyclase protein in the sample (e.g., an anti-adenylate cyclase antibody or an oligonucleotide probe that binds to DNA encoding an adenylate cyclase protein, e.g., SEQ ID NO:1). Kits can also include instructions for observing that the tested subject is suffering from or is at risk of developing a disorder associated with aberrant expression of adenylate cyclase sequences if the amount of adenylate cyclase protein or mRNA is above or below a normal level.

For antibody-based kits, the kit can comprise, for example: (1) a first antibody (e.g., attached to a solid support) that binds to adenylate cyclase protein; and, optionally, (2) a second, different antibody that binds to adenylate cyclase protein or the first antibody and is conjugated to a detectable agent. For oligonucleotide-based kits, the kit can comprise, for example: (1) an oligonucleotide, e.g., a detectably labeled oligonucleotide, that hybridizes to an adenylate cyclase nucleic acid sequence or (2) a pair of primers useful for amplifying an adenylate cyclase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of adenylate cyclase proteins.

2. Prognostic Assays

The methods described herein can furthermore be utilized as diagnostic or prognostic assays to identify subjects having or at risk of developing a disease or disorder associated with adenylate cyclase protein, adenylate cyclase nucleic acid expression, or adenylate cyclase activity. Prognostic assays can be used for prognostic or predictive purposes to thereby prophylactically treat an individual prior to the onset of a disorder characterized by or associated with adenylate cyclase protein, adenylate cyclase nucleic acid expression, or adenylate cyclase activity.

Thus, the present invention provides a method in which a test sample is obtained from a subject, and adenylate cyclase protein or nucleic acid (e.g., mRNA, genomic DNA) is detected, wherein the presence of adenylate cyclase protein or nucleic acid is diagnostic for a subject having or at risk of developing a disease or disorder associated with aberrant adenylate cyclase expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease adenylate cyclase activity) to effectively treat a disease or disorder associated with aberrant adenylate cyclase expression or activity. In this manner, a test sample is obtained and adenylate cyclase protein or nucleic acid is detected. The presence of adenylate cyclase protein or nucleic acid is diagnostic for a subject that can be administered the agent to treat a disorder associated with aberrant adenylate cyclase expression or activity.

The methods of the invention can also be used to detect genetic lesions or mutations in an adenylate cyclase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding an adenylate cyclase-protein, or the misexpression of the adenylate cyclase gene. For example, such genetic lesions or mutations can be detected by ascertaining the existence of at least one of: (1) a deletion of one or more nucleotides from an adenylate cyclase gene; (2) an addition of one or more nucleotides to an adenylate cyclase gene; (3) a substitution of one or more nucleotides of an adenylate cyclase gene; (4) a chromosomal rearrangement of an adenylate cyclase gene; (5) an alteration in the level of a messenger RNA transcript of an adenylate cyclase gene; (6) an aberrant modification of an adenylate cyclase gene, such as of the methylation pattern of the genomic DNA; (7) the presence of a non-wild-type splicing pattern of a messenger RNA transcript of an adenylate cyclase gene; (8) a non-wild-type level of an adenylate cyclase-protein; (9) an allelic loss of an adenylate cyclase gene; and (10) an inappropriate post-translational modification of an adenylate cyclase-protein. As described herein, there are a large number of assay techniques known in the art that can be used for detecting lesions in an adenylate cyclase gene. Any cell type or tissue, preferably peripheral blood leukocytes, in which adenylate cyclase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the adenylate cyclase gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an adenylate cyclase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in an adenylate cyclase molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the adenylate cyclase gene and detect mutations by comparing the sequence of the sample adenylate cyclase gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the adenylate cyclase gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in adenylate cyclase cDNAs obtained from samples of cells. See, e.g., Hsu et al. (1994) *Carcinogenesis* 15:1657–1662. According to an exemplary embodiment, a probe based on an adenylate cyclase sequence, e.g., a wild-type adenylate cyclase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in adenylate cyclase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving an adenylate cyclase gene.

3. Pharmacogenomics

Agents, or modulators that have a stimulatory or inhibitory effect on adenylate cyclase activity (e.g., adenylate cyclase gene expression) as identified by a screening assay described herein, can be administered to individuals to treat (prophylactically or therapeutically) disorders associated with aberrant adenylate cyclase activity as well as to modulate the phenotype of an immune response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of adenylate cyclase protein, expression of adenylate cyclase nucleic acid, or mutation content of adenylate cyclase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of adenylate cyclase protein, expression of adenylate cyclase nucleic acid, or mutation content of adenylate cyclase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an adenylate cyclase modulator, such as a modulator identified by one of the exemplary screening assays described herein.

4. Monitoring of Effects During Clinical Trials

Monitoring the influence of agents (e.g., drugs, compounds) on the expression or activity of adenylate cyclase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease adenylate cyclase gene expression, protein levels, or protein activity, can be monitored in clinical trials of subjects exhibiting decreased or increased adenylate cyclase gene expression, protein levels, or protein activity. In such clinical trials, adenylate cyclase expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates adenylate cyclase activity (e.g., as identified in a screening assay described herein) can be identified. Thus, to study the effect of agents on cellular proliferation disorders, for example, in a clinical trial, cells can be isolated and RNA prepared and analyzed for the levels of expression of adenylate cyclase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of adenylate cyclase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of an adenylate cyclase protein, mRNA, or genomic DNA in the preadministration sample; (3) obtaining one or more postadministration samples from the subject; (4) detecting the level of expression or activity of the adenylate cyclase protein, mRNA, or genomic DNA in the postadministration samples; (5) comparing the level of expression or activity of the adenylate cyclase protein, mRNA, or genomic DNA in the preadministration sample with the adenylate cyclase protein, mRNA, or genomic DNA in the postadministration sample or samples; and (vi) altering the administration of the agent to the subject accordingly to bring about the desired effect, i.e., for example, an increase or a decrease in the expression or activity of an adenylate cyclase protein.

C. Methods of Treatment

The present invention provides for both prophylactic and therapeutic methods of treating a subject at risk of (or susceptible to) a disorder or having a disorder associated with aberrant adenylate cyclase expression or activity. Additionally, the compositions of the invention find use in the treatment of disorders described herein.

1. Prophylactic Methods

In one aspect, the invention provides a method for preventing in a subject a disease or condition associated with an aberrant adenylate cyclase expression or activity by administering to the subject an agent that modulates adenylate cyclase expression or at least one adenylate cyclase gene activity. Subjects at risk for a disease that is caused, or contributed to, by aberrant adenylate cyclase expression or activity can be identified by, for example, any or a combination of diagnostic or prognostic assays as described herein. Administration of a prophylactic agent can occur prior to the manifestation of symptoms characteristic of the adenylate cyclase aberrancy, such that a disease or disorder is prevented or, alternatively, delayed in its progression. Depending on the type of adenylate cyclase aberrancy, for example, an adenylate cyclase agonist or adenylate cyclase antagonist agent can be used for treating the subject. The appropriate agent can be determined based on screening assays described herein.

2. Therapeutic Methods

Another aspect of the invention pertains to methods of modulating adenylate cyclase expression or activity for therapeutic purposes. The modulatory method of the invention involves contacting a cell with an agent that modulates one or more of the activities of adenylate cyclase protein activity associated with the cell. An agent that modulates adenylate cyclase protein activity can be an agent as described herein, such as a nucleic acid or a protein, a naturally-occurring cognate ligand of an adenylate cyclase protein, a peptide, an adenylate cyclase peptidomimetic, or other small molecule. In one embodiment, the agent stimulates one or more of the biological activities of adenylate cyclase protein. Examples of such stimulatory agents include active adenylate cyclase protein and a nucleic acid molecule encoding an adenylate cyclase protein that has been introduced into the cell. In another embodiment, the agent inhibits one or more of the biological activities of adenylate cyclase protein. Examples of such inhibitory agents include antisense adenylate cyclase nucleic acid molecules and anti-adenylate cyclase antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an adenylate cyclase protein or nucleic acid molecule. In one embodiment, the method involves administering an agent (e.g., an agent identified by a screening assay described herein), or a combination of agents, that modulates (e.g., upregulates or downregulates) adenylate cyclase expression or activity. In another embodiment, the method involves administering an adenylate cyclase protein or nucleic acid molecule as therapy to compensate for reduced or aberrant adenylate cyclase expression or activity.

Stimulation of adenylate cyclase activity is desirable in situations in which an adenylate cyclase protein is abnormally downregulated and/or in which increased adenylate cyclase activity is likely to have a beneficial effect. Conversely, inhibition of adenylate cyclase activity is desirable in situations in which adenylate cyclase activity is abnormally upregulated and/or in which decreased adenylate cyclase activity is likely to have a beneficial effect.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

This invention is further illustrated by the following examples, which should not be construed as limiting.

Experimental

EXAMPLE 1

Isolation of h21529

Clone h21529 was isolated from a human spleen or heart cDNA library. The identified clone h21529 encodes a transcript of approximately 3.52 Kb (corresponding cDNA set forth in SEQ ID NO:1). The open reading frame (nucleotides 247–3477) of this transcript encodes a predicted 1077 amino acid protein (SEQ ID NO:2). This novel gene is preliminarily mapped to human chromosome 14 using the mapping panel Genebridge 4 human RH.

A search of the nucleotide and protein databases revealed that h21529 encodes a polypeptide that shares similarity with several adenylate cyclases, the greatest similarity being seen with the rat adenylate cyclase type IV protein (SP Accession Number P26770, SEQ ID NO:3). An alignment of the h21529 polypeptide with this rat protein is shown in FIG. 1. The alignment was generated using the Clustal method with PAM250 residue weight table and sequence identities were determined by pairwise alignment. This overall close similarity between the two sequences indicates h21529 is the human ortholog of the rat adenylate cyclase type IV.

EXAMPLE 2 mRNA Expression of Clone h21529

Expression of the novel h21529 adenylate cyclase was measured by TaqMan® quantitative PCR (Perkin Elmer Applied Biosystems) in cDNA prepared from the following normal human tissues: thymus, skeletal muscle, liver, lung, thyroid, heart, ovary, aorta, placenta, cervix, lymph node, vein, brain, esophagus, pancreas, kidney, brain, prostate, liver, spleen, breast, colon, tonsil, small intestine, fetal kidney, fetal liver, fetal heart, and testis.

Probes were designed by PrimerExpress software (PE Biosystems) based on the h21529 sequence. The primers and probes for expression analysis of h21529 and β-2 microglobulin were as follows:

| | |
|---|---|
| h21529 Forward Primer | AGCTGTGGCCCAGTTAATGG (SEQ ID NO:3) |
| h21529 Reverse Primer | CTTTGGCCCCTTCCAGGTT (SEQ ID NO:4) |
| h21529 TaqMan Probe | CTACCGACTGGCGGTCATTGCCAG (SEQ ID NO:5) |
| β-2 microglobulin Forward Primer | CACCCCCACTGAAAAAGATGA (SEQ ID NO:6) |
| β-2 microglobulin Reverse Primer | CTTAACTATCTTGGGCTGTGACAAAG (SEQ ID NO:7) |
| β-2 microglobulin TaqMan Probe | TATGCCTGCCGTGTGAACCACGTG (SEQ ID NO:8) |

The h21529 sequence probe was labeled using FAM (6-carboxyfluorescein), and the β2-microglobulin reference probe was labeled with a different fluorescent dye, VIC. The differential labeling of the target adenylate cyclase sequence and internal reference gene thus enabled measurement in the same well. Forward and reverse primers and the probes for both β2-microglobulin and the target h21529 sequence were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target h21529 sequence. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate h21529 expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the h21529 sequence is normalized by subtracting the Ct value of the β-2 microglobulin gene to obtain a $_\Delta$Ct value using the following formula: $_\Delta Ct = Ct_{h21529} - Ct_{\beta\text{-2 microglobulin}}$. Expression is then calibrated against a cDNA sample showing a comparatively low level of expression of the h21529 sequence. The $_\Delta$Ct value for the calibrator sample is then subtracted from $_\Delta$Ct for each tissue sample according to the following formula: $_{\Delta\Delta}Ct = {_\Delta Ct}_{sample} - {_\Delta Ct}_{calibrator}$. Relative expression is then calculated using the arithmetic formula given by $2^{-\Delta\Delta Ct}$. Expression of the target h21529 sequence in each of the tissues tested was then graphically represented as discussed in more detail below.

The mRNA for the putative adenylate cyclase h21529 is differentially expressed in all of the normal tissues tested (FIG. 7). There was significant expression in pancreas, vein, brain, heart, and skeletal muscle; moderate expression in cervix, fetal kidney, fetal heart, liver, placenta, thyroid, ovary, breast, aorta, and brain; and lower expression in lymph node, esophagus, kidney, lung, spleen, testis, small intestine, fetal liver, colon, prostate, thymus, and tonsil. These data indicate this novel adenylate cyclase has a widely dispersed pattern of expression, a characteristic in common with the rat adenylate cyclase IV homolog.

EXAMPLE 3 mRNA Expression of Clone h21529 in Human Cardiovascular Tissues mRNA was hybridized as discussed in Example 2 in the following cardiovascular tissues: aorta, aorta with intimal proliferation, coronary artery, mammary internal artery, heart, congestive heart failure heart samples, ischemic heart samples, myopathic heart samples, and saphenous vein. These were compared in terms of relative expression to the expression of the gene in skeletal muscle. Highest expression was observed in tissue from congestive heart failure patients and myopathic hearts. Significant expression was also observed in coronary artery and in the internal mammary artery. Further, significant expression was also observed in ischemic heart. Lower levels of expression were observed in the remainder of the tissues. See FIG. 10.

Further, in situ hybridization experiments were done against hypertrophic cardiac myocytes from diseased hearts. Results showed increased expression of the gene in the hypertrophic myocytes.

SEQUENCE LISTING

<160> NUMBER OF SEQ ID NOS: 8

<210> SEQ ID NO 1
<211> LENGTH: 1077
<212> TYPE: PRT
<213> ORGANISM: Homo sapiens

<400> SEQUENCE: 1

```
Met Ala Arg Leu Phe Ser Pro Arg Pro Pro Ser Glu Asp Leu Phe
 1               5                  10                  15

Tyr Glu Thr Tyr Tyr Ser Leu Ser Gln Gln Tyr Pro Leu Leu Leu Leu
                20                  25                  30

Leu Leu Gly Ile Val Leu Cys Ala Leu Ala Ala Leu Leu Ala Val Ala
            35                  40                  45

Trp Ala Ser Gly Arg Glu Leu Thr Ser Asp Pro Ser Phe Leu Thr Thr
     50                  55                  60

Val Leu Cys Ala Leu Gly Gly Phe Ser Leu Leu Leu Gly Leu Ala Ser
65                  70                  75                  80

Arg Glu Gln Arg Leu Gln Arg Trp Thr Arg Pro Leu Ser Gly Leu Val
                85                  90                  95

Trp Val Ala Leu Leu Ala Leu Gly His Ala Phe Leu Phe Thr Gly Gly
            100                 105                 110

Val Val Ser Ala Trp Asp Gln Val Ser Tyr Phe Leu Phe Val Ile Phe
        115                 120                 125

Thr Ala Tyr Ala Met Leu Pro Leu Gly Met Arg Asp Ala Ala Val Ala
    130                 135                 140

Gly Leu Ala Ser Ser Leu Ser His Leu Leu Val Leu Gly Leu Tyr Leu
145                 150                 155                 160

Gly Pro Gln Pro Asp Ser Arg Pro Ala Leu Leu Pro Gln Leu Ala Ala
                165                 170                 175

Asn Ala Val Leu Phe Leu Cys Gly Asn Val Ala Gly Val Tyr His Lys
            180                 185                 190

Ala Leu Met Glu Arg Ala Leu Arg Ala Thr Phe Arg Glu Ala Leu Ser
        195                 200                 205
```

```
Ser Leu His Ser Arg Arg Leu Asp Thr Glu Lys Lys His Gln Glu
    210                 215                 220
His Leu Leu Leu Ser Ile Leu Pro Ala Tyr Leu Ala Arg Glu Met Lys
225                 230                 235                 240
Ala Glu Ile Met Ala Arg Leu Gln Ala Gly Gln Gly Ser Arg Pro Glu
            245                 250                 255
Ser Thr Asn Asn Phe His Ser Leu Tyr Val Lys Arg His Gln Gly Val
                260                 265                 270
Ser Val Leu Tyr Ala Asp Ile Val Gly Phe Thr Arg Leu Ala Ser Glu
        275                 280                 285
Cys Ser Pro Lys Glu Leu Val Leu Met Leu Asn Glu Leu Phe Gly Lys
290                 295                 300
Phe Asp Gln Ile Ala Lys Glu His Glu Cys Met Arg Ile Lys Ile Leu
305                 310                 315                 320
Gly Asp Cys Tyr Tyr Cys Val Ser Gly Leu Pro Leu Ser Leu Pro Asp
            325                 330                 335
His Ala Ile Asn Cys Val Arg Met Gly Leu Asp Met Cys Arg Ala Ile
                340                 345                 350
Arg Lys Leu Arg Ala Ala Thr Gly Val Asp Ile Asn Met Arg Val Gly
        355                 360                 365
Val His Ser Gly Ser Val Leu Cys Gly Val Ile Gly Leu Gln Lys Trp
370                 375                 380
Gln Tyr Asp Val Trp Ser His Asp Val Thr Leu Ala Asn His Met Glu
385                 390                 395                 400
Ala Gly Gly Val Pro Gly Arg Val His Ile Thr Gly Ala Thr Leu Ala
            405                 410                 415
Leu Leu Ala Gly Ala Tyr Ala Val Glu Asp Ala Gly Met Glu His Arg
                420                 425                 430
Asp Pro Tyr Leu Arg Glu Leu Gly Glu Pro Thr Tyr Leu Val Ile Asp
        435                 440                 445
Pro Arg Ala Glu Glu Asp Glu Lys Gly Thr Ala Gly Gly Leu Leu
450                 455                 460
Ser Ser Leu Glu Gly Leu Lys Met Arg Pro Ser Leu Leu Met Thr Arg
465                 470                 475                 480
Tyr Leu Glu Ser Trp Gly Ala Ala Lys Pro Phe Ala His Leu Ser His
            485                 490                 495
Gly Asp Ser Pro Val Ser Thr Thr Pro Leu Pro Glu Lys Thr Leu
                500                 505                 510
Ala Ser Phe Ser Thr Gln Trp Ser Leu Asp Arg Ser Arg Thr Pro Arg
        515                 520                 525
Gly Leu Asp Asp Glu Leu Asp Thr Gly Asp Ala Lys Phe Phe Gln Val
530                 535                 540
Ile Glu Gln Leu Asn Ser Gln Lys Gln Trp Lys Gln Ser Lys Asp Phe
545                 550                 555                 560
Asn Pro Leu Thr Leu Tyr Phe Arg Glu Lys Glu Met Glu Lys Glu Tyr
            565                 570                 575
Arg Leu Ser Ala Ile Pro Ala Phe Lys Tyr Tyr Glu Ala Cys Thr Phe
                580                 585                 590
Leu Val Phe Leu Ser Asn Phe Ile Ile Gln Met Leu Val Thr Asn Arg
        595                 600                 605
Pro Pro Ala Leu Ala Ile Thr Tyr Ser Ile Thr Phe Leu Leu Phe Leu
610                 615                 620
```

-continued

```
Leu Ile Leu Phe Val Cys Phe Ser Glu Asp Leu Met Arg Cys Val Leu
625                 630                 635                 640

Lys Gly Pro Lys Met Leu His Trp Leu Pro Ala Leu Ser Gly Leu Val
            645                 650                 655

Ala Thr Arg Pro Gly Leu Arg Ile Ala Leu Gly Thr Ala Thr Ile Leu
        660                 665                 670

Leu Val Phe Ala Met Ala Ile Thr Ser Leu Phe Phe Pro Thr Ser
    675                 680                 685

Ser Asp Cys Pro Phe Gln Ala Pro Asn Val Ser Ser Met Ile Ser Asn
690                 695                 700

Leu Ser Trp Glu Leu Pro Gly Ser Leu Pro Leu Ile Ser Val Pro Tyr
705                 710                 715                 720

Ser Met His Cys Cys Thr Leu Gly Phe Leu Ser Cys Ser Leu Phe Leu
                725                 730                 735

His Met Ser Phe Glu Leu Lys Leu Leu Leu Leu Leu Trp Leu Ala
            740                 745                 750

Ala Ser Cys Ser Leu Phe Leu His Ser His Ala Trp Leu Ser Glu Cys
        755                 760                 765

Leu Ile Val Arg Leu Tyr Leu Gly Pro Leu Asp Ser Arg Pro Gly Val
770                 775                 780

Leu Lys Glu Pro Lys Leu Met Gly Ala Ile Ser Phe Phe Ile Phe Phe
785                 790                 795                 800

Phe Thr Leu Leu Val Leu Ala Arg Gln Asn Glu Tyr Tyr Cys Arg Leu
                805                 810                 815

Asp Phe Leu Trp Lys Lys Leu Arg Gln Glu Arg Glu Thr Glu
            820                 825                 830

Thr Met Glu Asn Leu Thr Arg Leu Leu Glu Asn Val Leu Pro Ala
        835                 840                 845

His Val Ala Pro Gln Phe Ile Gly Gln Asn Arg Arg Asn Glu Asp Leu
    850                 855                 860

Tyr His Gln Ser Tyr Glu Cys Val Cys Val Leu Phe Ala Ser Val Pro
865                 870                 875                 880

Asp Phe Lys Glu Phe Tyr Ser Glu Ser Asn Ile Asn His Glu Gly Leu
                885                 890                 895

Glu Cys Leu Arg Leu Leu Asn Glu Ile Ile Ala Asp Phe Asp Glu Leu
            900                 905                 910

Leu Ser Lys Pro Lys Phe Ser Gly Val Glu Lys Ile Lys Thr Ile Gly
        915                 920                 925

Ser Thr Tyr Met Ala Ala Thr Gly Leu Asn Ala Thr Ser Gly Gln Asp
    930                 935                 940

Ala Gln Gln Asp Ala Glu Arg Ser Cys Ser His Leu Gly Thr Met Val
945                 950                 955                 960

Glu Phe Ala Val Ala Leu Gly Ser Lys Leu Asp Val Ile Asn Lys His
                965                 970                 975

Ser Phe Asn Asn Phe Arg Leu Arg Val Gly Leu Asn His Gly Pro Val
            980                 985                 990

Val Ala Gly Val Ile Gly Ala Gln Lys Pro Gln Tyr Asp Ile Trp Gly
        995                 1000                1005

Asn Thr Val Asn Val Ala Ser Arg Met Glu Ser Thr Gly Val Leu Gly
    1010                1015                1020

Lys Ile Gln Val Thr Glu Glu Thr Ala Trp Ala Leu Gln Ser Leu Gly
1025                1030                1035                1040

Tyr Thr Cys Tyr Ser Arg Gly Val Ile Lys Val Lys Gly Lys Gly Gln
```

-continued

```
                    1045                1050                1055
Leu Cys Thr Tyr Phe Leu Asn Thr Asp Leu Thr Arg Thr Gly Pro Pro
            1060                1065                1070

Ser Ala Thr Leu Gly
        1075

<210> SEQ ID NO 2
<211> LENGTH: 3518
<212> TYPE: DNA
<213> ORGANISM: Homo sapiens
<220> FEATURE:
<221> NAME/KEY: misc_feature
<222> LOCATION: (0)...(0)
<223> OTHER INFORMATION: 21529 adenylate cyclase
<220> FEATURE:
<221> NAME/KEY: CDS
<222> LOCATION: (247)...(3480)

<400> SEQUENCE: 2
cttctacaat cggggtttga ggaagaagaa gaaaaggact gaaggatccc ttcatcgcca      60
gctggaagcg ggcttgggag cccgcaagga gggcctgaaa agaagacgg gattgccaca     120 aggttggggg cgcggggtgg tacggctttg agcgggtgag aaaagctcag gtggggcccg    180
ccgggccgaa ggaggtaacc cggcgccggg ccctagccag ccccggggct cggggctggg    240 gagatc atg gcc cgc ctc ttc agc ccc cgg ccg ccc ccc agc gaa gac       288
       Met Ala Arg Leu Phe Ser Pro Arg Pro Pro Pro Ser Glu Asp
         1               5                  10 ctc ttc tac gag acc tac tac agc ctg agc cag cag tac ccg ctg ctg      336
Leu Phe Tyr Glu Thr Tyr Tyr Ser Leu Ser Gln Gln Tyr Pro Leu Leu
 15                  20                  25                  30 ctg ctg ctg ctg ggg atc gtg ctc tgt gcg ctc gcg gcg ctg ctc gca      384
Leu Leu Leu Leu Gly Ile Val Leu Cys Ala Leu Ala Ala Leu Leu Ala
             35                  40                  45 gtg gcc tgg gcc agc ggc agg gag ctg acc tca gac ccg agc ttc ctg      432
Val Ala Trp Ala Ser Gly Arg Glu Leu Thr Ser Asp Pro Ser Phe Leu
         50                  55                  60 acc act gtg ctg tgc gcg ctg ggc ggc ttc tcg ctg ctg ctg ggc ctc      480
Thr Thr Val Leu Cys Ala Leu Gly Gly Phe Ser Leu Leu Leu Gly Leu
     65                  70                  75 gct tcc cgg gag cag cga ctg cag cgc tgg acg cgt ccc ctg tcc ggc      528
Ala Ser Arg Glu Gln Arg Leu Gln Arg Trp Thr Arg Pro Leu Ser Gly
 80                  85                  90 ttg gta tgg gtc gcg ctg cta gcg cta ggc cac gcc ttc ctg ttc acc      576
Leu Val Trp Val Ala Leu Leu Ala Leu Gly His Ala Phe Leu Phe Thr
 95                 100                 105                 110 ggg ggc gtg gtg agc gcc tgg gac cag gtg tcc tat ttt ctc ttc gtc      624
Gly Gly Val Val Ser Ala Trp Asp Gln Val Ser Tyr Phe Leu Phe Val
            115                 120                 125 atc ttc acg gcg tat gcc atg ctg ccc ttg ggc atg cgg gac gcc gcc      672
Ile Phe Thr Ala Tyr Ala Met Leu Pro Leu Gly Met Arg Asp Ala Ala
        130                 135                 140 gtc gcg ggc ctc gcc tcc tca ctc tcg cat ctg ctg gtc ctc ggg ctg      720
Val Ala Gly Leu Ala Ser Ser Leu Ser His Leu Leu Val Leu Gly Leu
    145                 150                 155 tat ctt ggg cca cag ccg gac tca cgg cct gca ctg ctg ccg cag ttg      768
Tyr Leu Gly Pro Gln Pro Asp Ser Arg Pro Ala Leu Leu Pro Gln Leu
160                 165                 170 gca gca aac gca gtg ctg ttc ctg tgc ggg aac gtg gca gga gtg tac      816
Ala Ala Asn Ala Val Leu Phe Leu Cys Gly Asn Val Ala Gly Val Tyr
175                 180                 185                 190
```

```
cac aag gcg ctg atg gag cgc gcc ctg cgg gcc acg ttc cgg gag gca      864
His Lys Ala Leu Met Glu Arg Ala Leu Arg Ala Thr Phe Arg Glu Ala
            195                 200                 205 ctc agc tcc ctg cac tca cgc cgg cgg ctg gac acc gag aag aag cac      912
Leu Ser Ser Leu His Ser Arg Arg Arg Leu Asp Thr Glu Lys Lys His
        210                 215                 220 caa gaa cac ctt ctc ttg tcc atc ctt cct gcc tac ctg gcc cga gag      960
Gln Glu His Leu Leu Leu Ser Ile Leu Pro Ala Tyr Leu Ala Arg Glu
            225                 230                 235 atg aag gca gag atc atg gca cgg ctg cag gca gga cag ggg tca cgg     1008
Met Lys Ala Glu Ile Met Ala Arg Leu Gln Ala Gly Gln Gly Ser Arg
240                 245                 250 cca gag agc act aac aat ttc cac agc ctc tat gtc aag agg cac cag     1056
Pro Glu Ser Thr Asn Asn Phe His Ser Leu Tyr Val Lys Arg His Gln
255                 260                 265                 270 gga gtc agc gtg ctg tat gct gac atc gtg ggc ttc acg cgg ctg gcc     1104
Gly Val Ser Val Leu Tyr Ala Asp Ile Val Gly Phe Thr Arg Leu Ala
            275                 280                 285 agc gag tgt tcc cct aag gag ctg gtg ctc atg ctc aat gag ctc ttt     1152
Ser Glu Cys Ser Pro Lys Glu Leu Val Leu Met Leu Asn Glu Leu Phe
        290                 295                 300 ggc aag ttc gac cag att gcc aag gag cat gaa tgc atg cgg atc aag     1200
Gly Lys Phe Asp Gln Ile Ala Lys Glu His Glu Cys Met Arg Ile Lys
            305                 310                 315 atc ctg ggg gac tgt tac tac tgt gtc tct ggg ctg cca ctc tca ctg     1248
Ile Leu Gly Asp Cys Tyr Tyr Cys Val Ser Gly Leu Pro Leu Ser Leu
320                 325                 330 cca gac cat gcc atc aac tgc gtg cgc atg ggc ctg gac atg tgc cgg     1296
Pro Asp His Ala Ile Asn Cys Val Arg Met Gly Leu Asp Met Cys Arg
335                 340                 345                 350 gcc atc agg aaa ctg cgg gca gcc act ggc gtg gac atc aac atg cgt     1344
Ala Ile Arg Lys Leu Arg Ala Ala Thr Gly Val Asp Ile Asn Met Arg
            355                 360                 365 gtg ggc gtg cac tca ggc agc gta ctg tgt gga gtc atc ggg ctg cag     1392
Val Gly Val His Ser Gly Ser Val Leu Cys Gly Val Ile Gly Leu Gln
        370                 375                 380 aag tgg cag tac gac gtt tgg tca cat gat gtc aca ctg gct aac cac     1440
Lys Trp Gln Tyr Asp Val Trp Ser His Asp Val Thr Leu Ala Asn His
            385                 390                 395 atg gag gca ggc ggt gta cca ggg cga gtg cac atc aca ggg gct acc     1488
Met Glu Ala Gly Gly Val Pro Gly Arg Val His Ile Thr Gly Ala Thr
400                 405                 410 ctg gcc ctg ctg gca ggg gct tat gct gtg gag gac gca ggc atg gag     1536
Leu Ala Leu Leu Ala Gly Ala Tyr Ala Val Glu Asp Ala Gly Met Glu
415                 420                 425                 430 cat cgg gac ccc tac ctt cgg gag cta ggg gag cct acc tat ctg gtc     1584
His Arg Asp Pro Tyr Leu Arg Glu Leu Gly Glu Pro Thr Tyr Leu Val
            435                 440                 445 atc gat cca cgg gca gag gag gag gat gag aag ggc act gca gga ggc     1632
Ile Asp Pro Arg Ala Glu Glu Glu Asp Glu Lys Gly Thr Ala Gly Gly
        450                 455                 460 ttg ctg tcc tcg ctt gag ggc ctc aag atg cgt cca tca ctg ctg atg     1680
Leu Leu Ser Ser Leu Glu Gly Leu Lys Met Arg Pro Ser Leu Leu Met
            465                 470                 475 acc cgt tac ctg gag tcc tgg ggg gca gcc aag cct ttt gcc cac ctg     1728
Thr Arg Tyr Leu Glu Ser Trp Gly Ala Ala Lys Pro Phe Ala His Leu
480                 485                 490 agc cac gga gac agc cct gtg tcc acc tcc acc cct ctc ccg gag aag     1776
Ser His Gly Asp Ser Pro Val Ser Thr Ser Thr Pro Leu Pro Glu Lys
495                 500                 505                 510
```

```
acc ctg gct tcc ttc agc acc cag tgg agc ctg gat cgg agc cgt acc    1824
Thr Leu Ala Ser Phe Ser Thr Gln Trp Ser Leu Asp Arg Ser Arg Thr
            515                 520                 525 ccc cgg gga cta gat gat gaa ctg gac acc ggg gat gcc aag ttc ttc    1872
Pro Arg Gly Leu Asp Asp Glu Leu Asp Thr Gly Asp Ala Lys Phe Phe
            530                 535                 540 cag gtc att gag cag ctc aac tcg cag aaa cag tgg aag cag tcg aag    1920
Gln Val Ile Glu Gln Leu Asn Ser Gln Lys Gln Trp Lys Gln Ser Lys
            545                 550                 555 gac ttc aac cca ctg aca ctg tac ttc aga gag aag gag atg gag aaa    1968
Asp Phe Asn Pro Leu Thr Leu Tyr Phe Arg Glu Lys Glu Met Glu Lys
            560                 565                 570 gag tac cga ctc tct gca atc ccc gcc ttc aaa tac tat gaa gcc tgc    2016
Glu Tyr Arg Leu Ser Ala Ile Pro Ala Phe Lys Tyr Tyr Glu Ala Cys
575                 580                 585                 590 acc ttc ctg gtt ttt ctc tcc aac ttc atc atc cag atg cta gtg aca    2064
Thr Phe Leu Val Phe Leu Ser Asn Phe Ile Ile Gln Met Leu Val Thr
                595                 600                 605 aac agg ccc cca gct ctg gcc atc acg tat agc atc act ttc ctc ctc    2112
Asn Arg Pro Pro Ala Leu Ala Ile Thr Tyr Ser Ile Thr Phe Leu Leu
            610                 615                 620 ttc ctc ctc atc ctt ttt gtc tgc ttc tca gag gac ctg atg agg tgt    2160
Phe Leu Leu Ile Leu Phe Val Cys Phe Ser Glu Asp Leu Met Arg Cys
            625                 630                 635 gtc ctg aaa ggc ccc aag atg ctg cac tgg ctg cct gca ctg tct ggc    2208
Val Leu Lys Gly Pro Lys Met Leu His Trp Leu Pro Ala Leu Ser Gly
640                 645                 650 ctg gtg gcc aca cga cca gga ctg aga ata gcc ttg ggc acc gcc acc    2256
Leu Val Ala Thr Arg Pro Gly Leu Arg Ile Ala Leu Gly Thr Ala Thr
655                 660                 665                 670 atc ctc ctt gtc ttt gcc atg gcc att acc agc ctg ttc ttc ttc cca    2304
Ile Leu Leu Val Phe Ala Met Ala Ile Thr Ser Leu Phe Phe Phe Pro
                675                 680                 685 aca tca tca gac tgc cct ttc caa gct ccc aat gtg tcc tcc atg att    2352
Thr Ser Ser Asp Cys Pro Phe Gln Ala Pro Asn Val Ser Ser Met Ile
            690                 695                 700 tcc aac ctc tcc tgg gag ctc cct ggg tct ctg cct ctc atc agt gtc    2400
Ser Asn Leu Ser Trp Glu Leu Pro Gly Ser Leu Pro Leu Ile Ser Val
            705                 710                 715 cca tac tcc atg cac tgc tgc acg ctg ggc ttc ctc tcc tgc tcc ctc    2448
Pro Tyr Ser Met His Cys Cys Thr Leu Gly Phe Leu Ser Cys Ser Leu
            720                 725                 730 ttt ctg cac atg agc ttc gag ctg aag ctg ctg ctc ctg ctg tgg        2496
Phe Leu His Met Ser Phe Glu Leu Lys Leu Leu Leu Leu Leu Trp
735                 740                 745                 750 ctg gcg gca tcc tgc tcc ctc ttc ctg cac tcc cat gcc tgg ctg tcg    2544
Leu Ala Ala Ser Cys Ser Leu Phe Leu His Ser His Ala Trp Leu Ser
                755                 760                 765 gaa tgc ctc atc gtc cgc ctc tat ctg ggc ccc ttg gac tcc agg ccc    2592
Glu Cys Leu Ile Val Arg Leu Tyr Leu Gly Pro Leu Asp Ser Arg Pro
            770                 775                 780 gga gtg ctg aag gag ccc aaa ctg atg ggt gct atc tcc ttc ttc atc    2640
Gly Val Leu Lys Glu Pro Lys Leu Met Gly Ala Ile Ser Phe Phe Ile
            785                 790                 795 ttc ttc ttc acc ctc ctt gtc ctg gct cgc cag aat gag tac tac tgc    2688
Phe Phe Phe Thr Leu Leu Val Leu Ala Arg Gln Asn Glu Tyr Tyr Cys
            800                 805                 810 cgc ctg gac ttc ctg tgg aag aag aag ctg agg cag gag agg gag gag    2736
Arg Leu Asp Phe Leu Trp Lys Lys Lys Leu Arg Gln Glu Arg Glu Glu
```

```
                                                              -continued
815                    820                    825                    830 aca gag acg atg gag aac ctg act cgg ctg ctc ttg gag aac gtg ctc                2784
Thr Glu Thr Met Glu Asn Leu Thr Arg Leu Leu Leu Glu Asn Val Leu
                    835                    840                    845 cct gca cac gtg gcc ccc cag ttc att ggc cag aac cgg cgc aac gag                2832
Pro Ala His Val Ala Pro Gln Phe Ile Gly Gln Asn Arg Arg Asn Glu
            850                    855                    860 gat ctc tac cac cag tcc tat gaa tgc gtt tgt gtc ctc ttc gcc tca                2880
Asp Leu Tyr His Gln Ser Tyr Glu Cys Val Cys Val Leu Phe Ala Ser
        865                    870                    875 gtc cca gac ttc aag gag ttc tac tct gaa tcc aac atc aat cat gag                2928
Val Pro Asp Phe Lys Glu Phe Tyr Ser Glu Ser Asn Ile Asn His Glu
    880                    885                    890 ggc cta gag tgt ctg agg ctg ctc aat gag ata att gct gat ttt gat                2976
Gly Leu Glu Cys Leu Arg Leu Leu Asn Glu Ile Ile Ala Asp Phe Asp
895                    900                    905                    910 gag ctg ctc tcc aag ccc aag ttc agt ggg gtg gag aag atc aag acc                3024
Glu Leu Leu Ser Lys Pro Lys Phe Ser Gly Val Glu Lys Ile Lys Thr
                    915                    920                    925 atc ggc agc acc tac atg gca gcc aca ggc tta aat gcc acc tct gga                3072
Ile Gly Ser Thr Tyr Met Ala Ala Thr Gly Leu Asn Ala Thr Ser Gly
            930                    935                    940 cag gat gca caa cag gat gct gaa cgg agc tgc agc cac ctt ggc act                3120
Gln Asp Ala Gln Gln Asp Ala Glu Arg Ser Cys Ser His Leu Gly Thr
        945                    950                    955 atg gtg gaa ttt gcc gtg gcc ctg ggg tct aag ctg gac gtc atc aac                3168
Met Val Glu Phe Ala Val Ala Leu Gly Ser Lys Leu Asp Val Ile Asn
    960                    965                    970 aag cat tca ttc aac aac ttc cgc ctg cga gtg ggg ttg aac cat gga                3216
Lys His Ser Phe Asn Asn Phe Arg Leu Arg Val Gly Leu Asn His Gly
975                    980                    985                    990 ccc gta gta gct gga gtt att ggg gcc cag aag ccg caa tat gac att                3264
Pro Val Val Ala Gly Val Ile Gly Ala Gln Lys Pro Gln Tyr Asp Ile
                    995                    1000                   1005 tgg ggc aac aca gtg aac gtg gcc agc cgc atg gag agt aca gga gtc                3312
Trp Gly Asn Thr Val Asn Val Ala Ser Arg Met Glu Ser Thr Gly Val
            1010                   1015                   1020 ctt ggc aaa atc caa gtg act gag gag aca gca tgg gcc cta cag tcc                3360
Leu Gly Lys Ile Gln Val Thr Glu Glu Thr Ala Trp Ala Leu Gln Ser
        1025                   1030                   1035 ctg ggc tac acc tgc tac agc cgg ggt gtc atc aag gtg aaa ggc aaa                3408
Leu Gly Tyr Thr Cys Tyr Ser Arg Gly Val Ile Lys Val Lys Gly Lys
    1040                   1045                   1050 ggg cag ctc tgc acc tac ttc ctg aac aca gac ttg aca cga act gga                3456
Gly Gln Leu Cys Thr Tyr Phe Leu Asn Thr Asp Leu Thr Arg Thr Gly
1055                   1060                   1065                   1070 cct cct tca gct acc cta ggc tga gattgcactc gccttctaag aacctcaata              3510
Pro Pro Ser Ala Thr Leu Gly *
                    1075 aagagact                                                                        3518

<210> SEQ ID NO 3
<211> LENGTH: 20
<212> TYPE: DNA
<213> ORGANISM: Artificial Sequence
<220> FEATURE:
<223> OTHER INFORMATION: h21529 Forward Primer

<400> SEQUENCE: 3
agctgtggcc cagttaatgg                                                            20
```

-continued

```
<210> SEQ ID NO 4
<211> LENGTH: 19
<212> TYPE: DNA
<213> ORGANISM: Artificial Sequence
<220> FEATURE:
<223> OTHER INFORMATION: h21529 Reverse Primer

<400> SEQUENCE: 4
ctttggcccc ttccaggtt                                             19

<210> SEQ ID NO 5
<211> LENGTH: 24
<212> TYPE: DNA
<213> ORGANISM: Artificial Sequence
<220> FEATURE:
<223> OTHER INFORMATION: h21529 TaqMan Probe

<400> SEQUENCE: 5
ctaccgactg gcggtcattg ccag                                       24

<210> SEQ ID NO 6
<211> LENGTH: 21
<212> TYPE: DNA
<213> ORGANISM: Artificial Sequence
<220> FEATURE:
<223> OTHER INFORMATION: Beta-2 microglobulin forward primer

<400> SEQUENCE: 6 caccccccact gaaaaagatg a                                         21

<210> SEQ ID NO 7
<211> LENGTH: 26
<212> TYPE: DNA
<213> ORGANISM: Artificial Sequence
<220> FEATURE:
<223> OTHER INFORMATION: Beta-2 microglobulin reverse primer

<400> SEQUENCE: 7
cttaactatc ttgggctgtg acaaag                                     26

<210> SEQ ID NO 8
<211> LENGTH: 24
<212> TYPE: DNA
<213> ORGANISM: Artificial Sequence
<220> FEATURE:
<223> OTHER INFORMATION: Beta-2 microglobulin TaqMan Probe

<400> SEQUENCE: 8
tatgcctgcc gtgtgaacca cgtg                                       24
```

What is claimed is:

1. A method for screening test compounds to identify a compound that binds to a polypeptide comprising an amino acid sequence selected from the group consisting of:
   a) the amino acid sequence of a sequence variant of the amino acid sequence set forth in SEQ ID NO:1, wherein said sequence variant has adenylate cyclase activity and is encoded by a nucleotide sequence having at least 75% overall sequence identity with the nucleotide sequence shown in SEQ ID NO:2;
   b) the amino acid sequence of a sequence variant of the amino acid sequence encoded by the cDNA insert of the plasmid deposited with the ATCC as Patent Deposit No. PTA-1661, wherein said sequence variant has adenylate cyclase activity and is encoded by a nucleotide sequence having at least 75% overall sequence identity with the nucleotide sequence of the cDNA insert of the plasmid deposited with the ATCC as Patent Deposit No. PTA-1661;
   c) the amino acid sequence of a fragment of the amino acid sequence set forth in SEQ ID NO:1, wherein said fragment has adenylate cyclase activity and consists of at least 100 contiguous amino acids of the amino acid sequence set forth in SEQ ID NO:1; and
   d) the amino acid sequence of a fragment of the amino acid sequence encoded by the cDNA insert of the plasmid deposited with the ATCC as Patent Deposit No. PTA-1661, wherein said fragment has adenylate cyclase activity and consists of at least 100 contiguous amino acids of the amino acid sequence encoded by the cDNA insert of the plasmid deposited with the ATCC as Patent Deposit No. PTA-1661; said method comprising contacting the test compound with the polypeptide or a cell expressing the polypeptide under conditions suitable for binding of the compound to the polypeptide and determining whether a complex is formed between the test compound and the polypeptide.

2. The method of claim 1, wherein said polypeptide comprises an amino acid sequence selected from the group consisting of:
   a) the amino acid sequence of a sequence variant of the amino acid sequence set forth in SEQ ID NO:1, wherein said sequence variant has adenylate cyclase activity and is encoded by a nucleotide sequence having at least 85% overall sequence identity with the nucleotide sequence shown in SEQ ID NO:2; and
   b) the amino acid sequence of a sequence variant of the amino acid sequence encoded by the cDNA insert of the plasmid deposited with the ATCC as Patent Deposit No. PTA-1661, wherein said sequence variant has adenylate cyclase activity and is encoded by a nucleotide sequence having at least 85% overall sequence identity with the nucleotide sequence of the cDNA insert of the plasmid deposited with the ATCC as Patent Deposit No. PTA-1661.

3. The method of claim 2, wherein said polypeptide comprises an amino acid sequence selected from the group consisting of:
   a) the amino acid sequence of a sequence variant of the amino acid sequence set forth in SEQ ID NO:1, wherein said sequence variant has adenylate cyclase activity and is encoded by a nucleotide sequence having at least 95% sequence identity with the nucleotide sequence shown in SEQ ID NO:2; and
   b) the amino acid sequence of a sequence variant of the amino acid sequence encoded by the cDNA insert of the plasmid deposited with the ATCC as Patent Deposit No. PTA-1661, wherein said sequence variant has adenylate cyclase activity and is encoded by a nucleotide sequence having at least 95% sequence identity with the nucleotide sequence of the cDNA insert of the plasmid deposited with the ATCC as Patent Deposit No. PTA-1661.

4. The method of claim 3, wherein said polypeptide comprises an amino acid sequence selected from the group consisting of:
   a) the amino acid sequence set forth in SEQ ID NO:1; and
   b) the amino acid sequence encoded by the cDNA insert of the plasmid deposited with the ATCC as Patent Deposit No. PTA-1661.

5. The method of claim 1, wherein said polypeptide comprises an amino acid sequence selected from the group consisting of:
   a) the amino acid sequence of a fragment of the amino acid sequence set forth in SEQ ID NO:1, wherein said fragment has adenylate cyclase activity and consists of at least 100 contiguous amino acids of the amino acid sequence set forth in SEQ ID NO:1; and
   b) the amino acid sequence of a fragment of the amino acid sequence encoded by the cDNA insert of the plasmid deposited with the ATCC as Patent Deposit No. PTA-1661, wherein said fragment has adenylate cyclase activity and consists of at least 100 contiguous amino acids of the amino acid sequence encoded by the cDNA insert of the plasmid deposited with the ATCC as Patent Deposit No. PTA-1661.

6. The method of claim 1, wherein a cell expressing the polypeptide is contacted.

7. The method of claim 1, wherein said polypeptide mediates a cAMP-mediated signal transduction pathway and the step of determining whether a complex is formed between the test compound and the polypeptide is performed by monitoring the cAMP-mediated signal transduction pathway.

8. The method of claim 1, wherein said polypeptide mediates a cAMP-mediated cellular response and the step of determining whether a complex is formed between the test compound and the polypeptide is performed by monitoring the cAMP-mediated cellular response.

9. The method of claim 1, wherein said step of contacting the test compound with the polypeptide or a cell expressing the polypeptide is performed in the presence of a competing compound that can interact with the polypeptide and said step of determining whether a complex is formed between the test compound and the polypeptide is performed by assaying for a decrease in the formation of a complex between the competing compound and the polypeptide.

* * * * *